United States Patent
Bagga et al.

(10) Patent No.: US 9,439,765 B2
(45) Date of Patent: *Sep. 13, 2016

(54) METHOD FOR SUBCHONDRAL TREATMENT OF JOINT PAIN USING IMPLANTABLE DEVICES

(71) Applicant: ZIMMER KNEE CREATIONS, INC., Exton, PA (US)

(72) Inventors: Charanpreet S. Bagga, Basking Ridge, NJ (US); Shaun B. Hanson, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/453,301

(22) Filed: Aug. 6, 2014

(65) Prior Publication Data

US 2014/0350685 A1 Nov. 27, 2014

Related U.S. Application Data

(63) Continuation of application No. 12/950,183, filed on Nov. 19, 2010, now Pat. No. 8,801,800.

(60) Provisional application No. 61/354,100, filed on Jun. 11, 2010, provisional application No. 61/263,170, filed on Nov. 20, 2009.

(51) Int. Cl.
*A61F 2/28* (2006.01)
*A61F 2/38* (2006.01)
(Continued)

(52) U.S. Cl.
CPC .................. *A61F 2/28* (2013.01); *A61B 17/68* (2013.01); *A61B 17/7098* (2013.01); *A61F 2/38* (2013.01); *A61F 2/4601* (2013.01);
(Continued)

(58) Field of Classification Search
CPC ..................... A61F 2/4601; A61F 2002/2835; A61F 2002/2839; A61F 2002/30179; A61F 2002/4631
See application file for complete search history.

(56) References Cited

U.S. PATENT DOCUMENTS 2,697,433 A 12/1954 Zehnder
3,913,187 A 10/1975 Okuida
(Continued)

FOREIGN PATENT DOCUMENTS

CN 101048111 A 10/2007
CN 101102724 A 1/2008
(Continued)

OTHER PUBLICATIONS

"U.S. Appl. No. 12/950,061, Final Office Action mailed Jul. 15, 2013", 7 pgs.
(Continued)

*Primary Examiner* — Marcia Watkins
(74) *Attorney, Agent, or Firm* — Schwegman Lundberg & Woessner, P.A.

(57) ABSTRACT

Implantable devices for the surgical treatment of bone, and particularly to a bone defect at a joint region, and even more particularly at the subchondral bone level of the joint region, are disclosed. The implantable devices may be formed of a bone material, and configured to serve the dual functions of providing mechanical strength and structural integrity to the area to be treated, while also facilitating the dispersal of a flowable material in the same area. Associated delivery tools are also provided.

15 Claims, 17 Drawing Sheets

(51) Int. Cl.
*A61F 2/46* (2006.01)
*A61B 17/68* (2006.01)
*A61B 17/70* (2006.01)
*A61F 2/30* (2006.01)

(52) U.S. Cl.
CPC ............... *A61F 2002/2835* (2013.01); *A61F 2002/2839* (2013.01); *A61F 2002/30062* (2013.01); *A61F 2002/30179* (2013.01); *A61F 2002/30224* (2013.01); *A61F 2002/30237* (2013.01); *A61F 2002/4631* (2013.01)

(56) References Cited

U.S. PATENT DOCUMENTS

| | | |
|---|---|---|
| 3,988,783 A | 11/1976 | Treace |
| 4,037,592 A | 7/1977 | Kronner |
| 4,108,165 A | 8/1978 | Kopp et al. |
| 4,360,012 A | 11/1982 | Mcharrie et al. |
| 4,653,487 A | 3/1987 | Maale |
| 4,781,182 A | 11/1988 | Purnell et al. |
| 4,815,454 A | 3/1989 | Dozier, Jr. |
| 4,834,757 A | 5/1989 | Brantigan |
| 4,883,048 A | 11/1989 | Purnell et al. |
| 4,911,153 A | 3/1990 | Border |
| 4,920,958 A | 5/1990 | Walt et al. |
| 4,964,861 A | 10/1990 | Agee et al. |
| 5,098,383 A | 3/1992 | Hemmy et al. |
| 5,163,940 A | 11/1992 | Bourque |
| 5,178,164 A | 1/1993 | Allen |
| 5,247,934 A | 9/1993 | Wehrli et al. |
| 5,298,254 A | 3/1994 | Prewett et al. |
| 5,324,295 A | 6/1994 | Shapiro |
| 5,342,363 A | 8/1994 | Richelsoph |
| 5,370,646 A | 12/1994 | Reese et al. |
| 5,439,684 A | 8/1995 | Prewett et al. |
| 5,458,602 A | 10/1995 | Goble et al. |
| 5,514,137 A | 5/1996 | Coutts |
| 5,556,429 A | 9/1996 | Felt |
| 5,595,193 A | 1/1997 | Walus et al. |
| 5,609,636 A | 3/1997 | Kohrs et al. |
| 5,618,549 A | 4/1997 | Patat et al. |
| 5,681,320 A | 10/1997 | McGuire |
| 5,741,266 A | 4/1998 | Moran et al. |
| 5,743,916 A | 4/1998 | Greenberg et al. |
| 5,755,809 A | 5/1998 | Cohen et al. |
| 5,766,221 A | 6/1998 | Benderev et al. |
| 5,827,289 A | 10/1998 | Reiley et al. |
| 5,868,749 A | 2/1999 | Reed |
| 5,888,220 A | 3/1999 | Felt et al. |
| 5,891,150 A | 4/1999 | Chan |
| 5,928,239 A | 7/1999 | Mirza |
| 5,968,047 A | 10/1999 | Reed |
| 5,968,050 A | 10/1999 | Torrie |
| 5,972,015 A | 10/1999 | Scribner et al. |
| 6,010,502 A | 1/2000 | Bagby |
| 6,036,696 A | 3/2000 | Lambrecht et al. |
| 6,039,742 A | 3/2000 | Krettek et al. |
| 6,048,346 A | 4/2000 | Reiley et al. |
| 6,066,154 A | 5/2000 | Reiley et al. |
| 6,110,211 A | 8/2000 | Weiss |
| 6,111,164 A | 8/2000 | Rainey et al. |
| 6,120,511 A | 9/2000 | Chan |
| 6,140,452 A | 10/2000 | Felt et al. |
| 6,143,030 A | 11/2000 | Schroder |
| 6,162,225 A | 12/2000 | Gertzman et al. |
| 6,214,013 B1 | 4/2001 | Lambrecht et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,254,605 B1 | 7/2001 | Howell |
| 6,267,770 B1 | 7/2001 | Truwit |
| 6,270,528 B1 | 8/2001 | Mckay |
| 6,283,942 B1 | 9/2001 | Staehlin et al. |
| 6,285,901 B1 | 9/2001 | Taicher et al. |
| 6,287,313 B1 | 9/2001 | Sasso |
| 6,294,187 B1 | 9/2001 | Boyce et al. |
| 6,306,177 B1 | 10/2001 | Felt et al. |
| 6,342,056 B1 | 1/2002 | Mac-Thiong et al. |
| 6,358,251 B1 | 3/2002 | Mirza |
| 6,368,322 B1 | 4/2002 | Luks et al. |
| 6,395,007 B1 | 5/2002 | Bhatnagar et al. |
| 6,398,811 B1 | 6/2002 | Mckay |
| 6,423,083 B2 | 7/2002 | Reiley et al. |
| 6,486,232 B1 | 11/2002 | Wise et al. |
| 6,506,192 B1 | 1/2003 | Gertzman et al. |
| 6,506,785 B2 | 1/2003 | Evans et al. |
| 6,520,969 B2 | 2/2003 | Lambrecht et al. |
| 6,527,773 B1 | 3/2003 | Lin et al. |
| 6,533,794 B2 | 3/2003 | Chakeres |
| 6,564,083 B2 | 5/2003 | Stevens |
| 6,607,561 B2 | 8/2003 | Brannon |
| 6,613,054 B2 | 9/2003 | Scribner et al. |
| 6,645,213 B2 | 11/2003 | Sand et al. |
| 6,663,647 B2 | 12/2003 | Reiley et al. |
| 6,719,761 B1 | 4/2004 | Reiley et al. |
| 6,726,691 B2 | 4/2004 | Osorio et al. |
| 6,730,124 B2 | 5/2004 | Steiner |
| 6,746,451 B2 | 6/2004 | Middleton et al. |
| 6,767,369 B2 | 7/2004 | Boyer, II et al. |
| 6,814,736 B2 | 11/2004 | Reiley et al. |
| 6,827,720 B2 | 12/2004 | Leali |
| 6,863,672 B2 | 3/2005 | Reiley et al. |
| 6,863,899 B2 | 3/2005 | Koblish et al. |
| 6,869,434 B2 | 3/2005 | Choi |
| 6,875,212 B2 | 4/2005 | Shaolian et al. |
| 6,887,246 B2 | 5/2005 | Bhatnagar et al. |
| 6,899,719 B2 | 5/2005 | Reiley et al. |
| 6,917,827 B2 | 7/2005 | Kienzle, III |
| 6,918,916 B2 | 7/2005 | Gobel et al. |
| 6,923,813 B2 | 8/2005 | Phillips |
| 6,979,341 B2 | 12/2005 | Scribner et al. |
| 6,981,981 B2 | 1/2006 | Reiley |
| 7,001,431 B2 | 2/2006 | Bao et al. |
| 7,029,477 B2 | 4/2006 | Grimm |
| 7,063,701 B2 | 6/2006 | Michelson |
| 7,063,702 B2 | 6/2006 | Michelson |
| 7,087,082 B2 | 8/2006 | Paul et al. |
| 7,094,239 B1 | 8/2006 | Michelson |
| 7,115,146 B2 | 10/2006 | Boyer, II et al. |
| 7,144,414 B2 | 12/2006 | Harvie et al. |
| 7,153,305 B2 | 12/2006 | Johnson et al. |
| 7,153,306 B2 | 12/2006 | Ralph et al. |
| 7,153,307 B2 | 12/2006 | Scribner |
| 7,155,306 B2 | 12/2006 | Haitin et al. |
| 7,160,305 B2 | 1/2007 | Schmieding |
| 7,192,431 B2 | 3/2007 | Hangody et al. |
| 7,226,481 B2 | 6/2007 | Kuslich |
| 7,241,303 B2 | 7/2007 | Reiss et al. |
| 7,250,055 B1 | 7/2007 | Vanderwalle |
| 7,252,671 B2 | 8/2007 | Scribner et al. |
| 7,261,716 B2 | 8/2007 | Strobel et al. |
| 7,261,720 B2 | 8/2007 | Stevens et al. |
| 7,313,430 B2 | 12/2007 | Urquhart et al. |
| 7,399,306 B2 | 7/2008 | Reiley et al. |
| 7,410,947 B2 | 8/2008 | Rueger et al. |
| 7,448,264 B2 | 11/2008 | Boyce et al. |
| 7,458,977 B2 | 12/2008 | McGinley et al. |
| 7,468,075 B2 | 12/2008 | Lang et al. |
| 7,476,226 B2 | 1/2009 | Weikel et al. |
| 7,477,770 B2 | 1/2009 | Wehrli et al. |
| 7,485,119 B2 | 2/2009 | Thelen et al. |
| 7,488,348 B2 | 2/2009 | Truncale et al. |
| 7,491,205 B1 | 2/2009 | Michelson |
| 7,507,240 B2 | 3/2009 | Olsen |
| 7,534,226 B2 | 5/2009 | Mernoe et al. |
| 7,545,964 B2 | 6/2009 | Lang et al. |
| 7,550,007 B2 | 6/2009 | Malinin |
| 7,550,011 B2 | 6/2009 | Mckay et al. |
| 7,556,295 B2 | 7/2009 | Holzheu |
| 7,559,932 B2 | 7/2009 | Truckai et al. |
| 7,575,578 B2 | 8/2009 | Wetzler et al. |
| 7,594,917 B2 | 9/2009 | Whittaker et al. |
| 7,608,097 B2 | 10/2009 | Kyle |

(56) References Cited

U.S. PATENT DOCUMENTS

| | | | |
|---|---|---|---|
| 7,608,098 B1 | 10/2009 | Stone | |
| 7,643,664 B2 | 1/2010 | Wehrli et al. | |
| 7,682,378 B2 | 3/2010 | Truckai et al. | |
| 7,704,256 B2 | 4/2010 | Sand et al. | |
| 7,708,742 B2 | 5/2010 | Scribner et al. | |
| 7,713,273 B2 | 5/2010 | Krueer et al. | |
| 7,731,720 B2 | 6/2010 | Sand et al. | |
| 7,753,963 B2 | 7/2010 | Boyer, II et al. | |
| 7,769,213 B2 | 8/2010 | Gregory et al. | |
| 7,771,431 B2 | 8/2010 | Scribner et al. | |
| 7,789,912 B2 | 9/2010 | Manzi et al. | |
| 7,811,290 B2 | 10/2010 | Rabiner | |
| 7,837,733 B2 | 11/2010 | Collins et al. | |
| 7,837,740 B2 | 11/2010 | Semler et al. | |
| 7,840,247 B2 | 11/2010 | Liew et al. | |
| 7,846,206 B2 | 12/2010 | Oglaza et al. | |
| 7,879,038 B2 | 2/2011 | Reiley et al. | |
| 7,879,099 B2 | 2/2011 | Zipnick | |
| 7,887,543 B2 | 2/2011 | Sand et al. | |
| 7,887,546 B2 | 2/2011 | Gil | |
| 7,896,885 B2 | 3/2011 | Miniaci et al. | |
| 7,901,408 B2 | 3/2011 | Ek | |
| 7,901,457 B2 | 3/2011 | Truncale et al. | |
| 7,905,924 B2 | 3/2011 | White | |
| 7,914,539 B2 | 3/2011 | Stone et al. | |
| 7,927,339 B2 | 4/2011 | Ralph et al. | |
| 7,931,840 B2 | 4/2011 | Michelson | |
| 7,938,835 B2 | 5/2011 | Boucher et al. | |
| 7,959,638 B2 | 6/2011 | Osorio et al. | |
| 7,985,231 B2 | 7/2011 | Sankaran | |
| 8,029,511 B2 | 10/2011 | Bowman et al. | |
| 8,062,364 B1 | 11/2011 | Sharkey et al. | |
| 8,070,753 B2 | 12/2011 | Truckai et al. | |
| 8,092,480 B2 | 1/2012 | Layne | |
| 8,133,226 B2 | 3/2012 | Chou et al. | |
| 8,142,462 B2 | 3/2012 | Middleton | |
| 8,152,813 B2 | 4/2012 | Osorio et al. | |
| 8,168,692 B2 | 5/2012 | Wenz | |
| 8,187,327 B2 | 5/2012 | Edidin et al. | |
| 8,246,681 B2 | 8/2012 | Osorio et al. | |
| 8,608,802 B2 | 12/2013 | Bagga et al. | |
| 8,617,166 B2 | 12/2013 | Hanson et al. | |
| 8,617,176 B2 | 12/2013 | Lizardi et al. | |
| 8,636,745 B2 | 1/2014 | Almutairi et al. | |
| 8,801,800 B2 | 8/2014 | Bagga et al. | |
| 8,821,504 B2 | 9/2014 | Sharkey et al. | |
| 8,864,768 B2 | 10/2014 | Hanson et al. | |
| 8,906,032 B2 | 12/2014 | Hanson et al. | |
| 8,951,261 B2 | 2/2015 | Sharkey et al. | |
| 9,033,987 B2 | 5/2015 | Hanson et al. | |
| 9,119,721 B2* | 9/2015 | Sharkey | A61B 17/1764 |
| 2002/0029084 A1 | 3/2002 | Paul et al. | |
| 2002/0151897 A1 | 10/2002 | Zirkie, Jr. | |
| 2003/0009235 A1 | 1/2003 | Manrique et al. | |
| 2003/0097135 A1 | 5/2003 | Penenberg | |
| 2003/0105468 A1 | 6/2003 | Gorek | |
| 2003/0138473 A1 | 7/2003 | Koblish et al. | |
| 2003/0220651 A1 | 11/2003 | Pusnik et al. | |
| 2003/0225456 A1 | 12/2003 | Ek | |
| 2004/0002759 A1 | 1/2004 | Ferree | |
| 2004/0010261 A1 | 1/2004 | Hoag et al. | |
| 2004/0106925 A1 | 6/2004 | Culbert | |
| 2004/0127987 A1 | 7/2004 | Evans et al. | |
| 2004/0167538 A1 | 8/2004 | Gerber et al. | |
| 2005/0075641 A1 | 4/2005 | Singhatat et al. | |
| 2005/0119219 A1 | 6/2005 | Bellini et al. | |
| 2005/0119753 A1 | 6/2005 | Mcgahan et al. | |
| 2005/0149022 A1 | 7/2005 | Shaolian et al. | |
| 2005/0159812 A1 | 7/2005 | Dinger, III et al. | |
| 2005/0177171 A1 | 8/2005 | Wetzler et al. | |
| 2005/0182418 A1 | 8/2005 | Boyd et al. | |
| 2005/0203622 A1 | 9/2005 | Steiner et al. | |
| 2005/0203623 A1 | 9/2005 | Steiner et al. | |
| 2005/0256527 A1 | 11/2005 | Delfosse et al. | |
| 2005/0267584 A1 | 12/2005 | Burdulis, Jr. et al. | |
| 2005/0288795 A1 | 12/2005 | Bagga et al. | |
| 2006/0052791 A1 | 3/2006 | Hagen et al. | |
| 2006/0064164 A1 | 3/2006 | Thelen et al. | |
| 2006/0084986 A1 | 4/2006 | Grinberg et al. | |
| 2006/0247642 A1 | 11/2006 | Stone et al. | |
| 2006/0271059 A1 | 11/2006 | Reay-young et al. | |
| 2007/0055280 A1 | 3/2007 | Osorio et al. | |
| 2007/0100462 A1 | 5/2007 | Lang et al. | |
| 2007/0127987 A1 | 6/2007 | Altenbuchner | |
| 2007/0225813 A1* | 9/2007 | Haines | A61B 17/8625 623/17.16 |
| 2007/0276370 A1 | 11/2007 | Altarac et al. | |
| 2007/0282346 A1 | 12/2007 | Scribner et al. | |
| 2008/0027434 A1 | 1/2008 | Zucherman et al. | |
| 2008/0039857 A1 | 2/2008 | Giersch et al. | |
| 2008/0039866 A1 | 2/2008 | Stetz et al. | |
| 2008/0077251 A1* | 3/2008 | Chen | A01N 1/02 623/23.72 |
| 2008/0103506 A1 | 5/2008 | Volpi et al. | |
| 2008/0195115 A1 | 8/2008 | Oren et al. | |
| 2008/0243127 A1 | 10/2008 | Lang et al. | |
| 2008/0281331 A1 | 11/2008 | Fritzinger et al. | |
| 2008/0288006 A1 | 11/2008 | Brannon | |
| 2008/0306490 A1 | 12/2008 | Lakin et al. | |
| 2009/0062797 A1 | 3/2009 | Huebner et al. | |
| 2009/0069901 A1 | 3/2009 | Truncale et al. | |
| 2009/0093813 A1 | 4/2009 | Elghazaly et al. | |
| 2009/0204158 A1 | 8/2009 | Sweeney | |
| 2010/0015202 A1 | 1/2010 | Semler et al. | |
| 2010/0076503 A1 | 3/2010 | Beyar et al. | |
| 2010/0145451 A1 | 6/2010 | Dee | |
| 2010/0160970 A1 | 6/2010 | Sevrain | |
| 2010/0179549 A1 | 7/2010 | Keller et al. | |
| 2010/0274254 A1 | 10/2010 | Boileau et al. | |
| 2011/0125156 A1 | 5/2011 | Sharkey et al. | |
| 2011/0125157 A1 | 5/2011 | Sharkey et al. | |
| 2011/0125159 A1 | 5/2011 | Hanson et al. | |
| 2011/0125160 A1 | 5/2011 | Bagga et al. | |
| 2011/0125200 A1 | 5/2011 | Hanson et al. | |
| 2011/0125201 A1 | 5/2011 | Hanson et al. | |
| 2011/0125264 A1 | 5/2011 | Bagga et al. | |
| 2011/0125265 A1 | 5/2011 | Bagga et al. | |
| 2011/0125272 A1 | 5/2011 | Bagga et al. | |
| 2014/0074103 A1* | 3/2014 | Mandeen | A61B 17/7097 606/93 |
| 2014/0107781 A1 | 4/2014 | Bagga et al. | |
| 2014/0114369 A1 | 4/2014 | Hanson et al. | |
| 2014/0350683 A1 | 11/2014 | Sharkey et al. | |
| 2015/0025589 A1 | 1/2015 | Hanson et al. | |
| 2015/0230807 A1 | 8/2015 | Hanson et al. | |
| 2015/0257886 A1* | 9/2015 | Sharkey | A61F 2/30 623/18.11 |

FOREIGN PATENT DOCUMENTS

| | | |
|---|---|---|
| CN | 101460105 A | 6/2009 |
| CN | 102770067 A | 11/2012 |
| CN | 102781348 A | 11/2012 |
| CN | 102740784 B | 9/2015 |
| EP | 2501303 A1 | 9/2012 |
| EP | 2501306 A1 | 9/2012 |
| EP | 2501314 A1 | 9/2012 |
| EP | 2501342 A1 | 9/2012 |
| WO | WO-03084412 A1 | 10/2003 |
| WO | WO-2005079881 A1 | 9/2005 |
| WO | WO-2008155772 A1 | 12/2008 |
| WO | WO-2011063240 A1 | 5/2011 |
| WO | WO-2011063250 A1 | 5/2011 |
| WO | WO-2011063257 A1 | 5/2011 |
| WO | WO-2011063267 A1 | 5/2011 |
| WO | WO-2011063279 A1 | 5/2011 |
| WO | WO-2011063281 A1 | 5/2011 |

OTHER PUBLICATIONS

"U.S. Appl. No. 12/950,061, Non Final Office Action mailed Feb. 7, 2013", 7 pgs.

"U.S. Appl. No. 12/950,061, Notice of Allowance mailed Oct. 1, 2013", 6 pgs.

(56) References Cited

OTHER PUBLICATIONS

"U.S. Appl. No. 12/950,061, Preliminary Amendment filed Feb. 8, 2011", 3 pgs.
"U.S. Appl. No. 12/950,061, Response filed Jun. 7, 2013 to Non Final Office Action mailed Feb. 7, 2013", 14 pgs.
"U.S. Appl. No. 12/950,061, Response filed Sep. 16, 2013 to Final Office Action mailed Jul. 15, 2013", 13 pgs.
"U.S. Appl. No. 12/950,097, Final Office Action mailed Dec. 10, 2013", 6 pgs.
"U.S. Appl. No. 12/950,097, Non Final Office Action mailed Feb. 15, 2013", 8 pgs.
"U.S. Appl. No. 12/950,097, Non Final Office Action mailed Aug. 6, 2013", 6 pgs.
"U.S. Appl. No. 12/950,097, Notice of Allowance mailed Apr. 2, 2014", 5 pgs.
"U.S. Appl. No. 12/950,097, Notice of Allowance mailed Jul. 9, 2014", 5 pgs.
"U.S. Appl. No. 12/950,097, Preliminary Amendment filed Feb. 7, 2011", 3 pgs.
"U.S. Appl. No. 12/950,097, Response filed Mar. 10, 2014 to Final Office Action mailed Dec. 10, 2013", 13 pgs.
"U.S. Appl. No. 12/950,097, Response filed Jun. 17, 2013 to Non Final Office Action mailed Feb. 15, 2013", 15 pgs.
"U.S. Appl. No. 12/950,097, Response filed Nov. 6, 2013 to Non Final Office Action mailed Aug. 6, 2013", 14 pgs.
"U.S. Appl. No. 12/950,114, Final Office Action mailed Jul. 15, 2013", 6 pgs.
"U.S. Appl. No. 12/950,114, Non Final Office Action mailed Feb. 6, 2014", 6 pgs.
"U.S. Appl. No. 12/950,114, Non Final Office Action mailed Mar. 7, 2013", 6 pgs.
"U.S. Appl. No. 12/950,114, Notice of Allowance mailed Jun. 16, 2014", 5 pgs.
"U.S. Appl. No. 12/950,114, Preliminary Amendment filed Feb. 8, 2011", 3 pgs.
"U.S. Appl. No. 12/950,114, Response filed May 6, 2014 to Non-Final Office Action mailed Feb. 6, 2014", 7 pgs.
"U.S. Appl. No. 12/950,114, Response filed Jun. 7, 2013 to Non Final Office Action mailed Mar. 7, 2013", 8 pgs.
"U.S. Appl. No. 12/950,114, Response filed Sep. 16, 2013 to Final Office Action mailed Jul. 15, 2013", 8 pgs.
"U.S. Appl. No. 12/950,154, Final Office Action mailed Aug. 8, 2013", 7 pgs.
"U.S. Appl. No. 12/950,154, Non Final Office Action mailed Feb. 25, 2014", 6 pgs.
"U.S. Appl. No. 12/950,154, Non Final Office Action mailed Mar. 15, 2013", 8 pgs.
"U.S. Appl. No. 12/950,154, Preliminary Amendment filed Feb. 7, 2011", 4 pgs.
"U.S. Appl. No. 12/950,154, Response filed Jun. 17, 2013 to Non Final Office Action mailed Mar. 15, 2013", 15 pgs.
"U.S. Appl. No. 12/950,154, Response filed Oct. 8, 2013 to Final Office Action mailed Aug. 8, 2013", 18 pgs.
"U.S. Appl. No. 12/950,183, Examiner Interview Summary mailed Feb. 13, 2014", 3 pgs.
"U.S. Appl. No. 12/950,183, Final Office Action mailed Oct. 30, 2012", 16 pgs.
"U.S. Appl. No. 12/950,183, Non Final Office Action mailed May 29, 2012", 10 pgs.
"U.S. Appl. No. 12/950,183, Non Final Office Action mailed Oct. 11, 2013", 12 pgs.
"U.S. Appl. No. 12/950,183, Notice of Allowance mailed Feb. 19, 2014", 5 pgs.
"U.S. Appl. No. 12/950,183, Notice of Allowance mailed Jun. 6, 2014", 7 pgs.
"U.S. Appl. No. 12/950,183, Preliminary Amendment filed Feb. 8, 2011", 4 pgs.
"U.S. Appl. No. 12/950,183, Response filed Jan. 13, 2014 to Non Final Office Action mailed Oct. 11, 2013", 11 pgs.
"U.S. Appl. No. 12/950,183, Response filed Apr. 30, 2013 to Final Office Action mailed Oct. 30, 2012", 11 pgs.
"U.S. Appl. No. 12/950,183, Response filed May 11, 2012 to Restriction Requirement mailed Apr. 13, 2012", 2 pgs.
"U.S. Appl. No. 12/950,183, Response filed Aug. 28, 2012 to Non Final Office Action mailed May 29, 2012", 10 pgs.
"U.S. Appl. No. 12/950,183, Restriction Requirement mailed Apr. 13, 2012", 8 pgs.
"U.S. Appl. No. 12/950,183, Supplemental Amendment filed Feb. 7, 2014", 8 pgs.
"U.S. Appl. No. 12/950,230, Final Office Action mailed Jan. 11, 2013", 10 pgs.
"U.S. Appl. No. 12/950,230, Non Final Office Action mailed Jul. 17, 2014", 10 pgs.
"U.S. Appl. No. 12/950,230, Non Final Office Action mailed Aug. 2, 2012", 9 pgs.
"U.S. Appl. No. 12/950,230, Preliminary Amendment filed Feb. 8, 2011", 3 pgs.
"U.S. Appl. No. 12/950,230, Response filed Apr. 11, 2013 to Final Office Action mailed Jan. 11, 2013", 10 pgs.
"U.S. Appl. No. 12/950,273, Final Office Action mailed Nov. 6, 2012", 9 pgs.
"U.S. Appl. No. 12/950,273, Non Final Office Action mailed Apr. 13, 2012", 15 pgs.
"U.S. Appl. No. 12/950,273, Non Final Office Action mailed Apr. 25, 2014", 12 pgs.
"U.S. Appl. No. 12/950,273, Preliminary Amendment filed Feb. 8, 2011", 3 pgs.
"U.S. Appl. No. 12/950,273, Response filed Mar. 6, 2013 to Final Office Action mailed Nov. 6, 2012", 10 pgs.
"U.S. Appl. No. 12/950,273, Response filed Jul. 12, 2012 to Non Final Office Action mailed Apr. 13, 2012", 12 pgs.
"U.S. Appl. No. 12/950,306, Final Office Action mailed Nov. 26, 2012", 9 pgs.
"U.S. Appl. No. 12/950,306, Non Final Office Action mailed Jun. 14, 2012", 11 pgs.
"U.S. Appl. No. 12/950,306, Notice of Allowance mailed May 28, 2013", 9 pgs.
"U.S. Appl. No. 12/950,306, Notice of Allowance mailed Aug. 13, 2013", 9 pgs.
"U.S. Appl. No. 12/950,306, Preliminary Amendment filed Feb. 8, 2011", 7 pgs.
"U.S. Appl. No. 12/950,306, Response filed Apr. 30, 2013 to Final Office Action mailed Nov. 26, 2012", 15 pgs.
"U.S. Appl. No. 12/950,306, Response filed Sep. 13, 2012 to Non Final Office Action mailed Jun. 14, 2012", 11 pgs.
"U.S. Appl. No. 12/950,355, Final Office Action mailed Mar. 12, 2013", 15 pgs.
"U.S. Appl. No. 12/950,355, Non Final Office Action mailed Jul. 29, 2014", 9 pgs.
"U.S. Appl. No. 12/950,355, Non Final Office Action mailed Aug. 13, 2012", 16 pgs.
"U.S. Appl. No. 12/950,355, Response filed Jan. 14, 2013 to Non Final Office Action mailed Aug. 13, 2012", 17 pgs.
"U.S. Appl. No. 12/950,355, Response filed Jul. 12, 2013 to Final Office Action mailed Mar. 12, 2013", 20 pgs.
"U.S. Appl. No. 14/143,883, Non Final Office Action mailed Aug. 4, 2014", 6 pgs.
"Chinese Application Serial No. 201080020717.2, Office Action mailed Jan. 9, 2014", (W/English Translation), 11 pgs.
"Chinese Application Serial No. 201080052569.2, Office Action mailed Apr. 25, 2014", w/English Translation, 17 pgs.
"Chinese Application Serial No. 201080052578.1, Office Action mailed Apr. 1, 2014", w/English Translation, 11 pgs.
"Chinese Application Serial No. 201080052580.9, Office Action mailed Apr. 3, 2014", w/English Translation, 18 pgs.
"Chinese Application Serial No. 201080052583.2, Office Action mailed Mar. 14, 2014", w/English Translation, 9 pgs.
"European Application Serial No. 10832277.7, Office Action mailed Jun. 27, 2012", 2 pgs.
"European Application Serial No. 10832285.0, Office Action mailed Jun. 27, 2012", 2 pgs.

(56) References Cited

OTHER PUBLICATIONS

"International Application Serial No. PCT/US2010/057426, International Preliminary Report on Patentability mailed May 22, 2012", 9 pgs.
"International Application Serial No. PCT/US2010/057426, International Search Report and Written Opinion mailed Jan. 24, 2011", 10 pgs.
"International Application Serial No. PCT/US2010/057440, International Preliminary Report on Patentability mailed May 22, 2012", 7 pgs.
"International Application Serial No. PCT/US2010/057440, International Search Report and Written Opinion mailed Feb. 7, 2011", 8 pgs.
"International Application Serial No. PCT/US2010/057456, International Preliminary Report on Patentability mailed May 22, 2012", 6 pgs.
"International Application Serial No. PCT/US2010/057456, International Search Report and Written Opinion mailed Jan. 14, 2011", 7 pgs.
"International Application Serial No. PCT/US2010/057471, International Preliminary Report on Patentability mailed May 31, 2012", 7 pgs.
"International Application Serial No. PCT/US2010/057471, International Search Report mailed Jan. 18, 2011", 2 pgs.
"International Application Serial No. PCT/US2010/057471, Written Opinion mailed Jan. 18, 2011", 5 ogs.
"International Application Serial No. PCT/US2010/057475, International Preliminary Report on Patentability mailed May 22, 2012", 6 pgs.
"International Application Serial No. PCT/US2010/057475, International Search Report mailed Jan. 18, 2011", 8 pgs.
"International Application Serial No. PCT/US2010/057475, Written Opinion mailed Jan. 18, 2011", 5 pgs.
"International Application Serial No. PCT/US2010/057483, International Preliminary Report on Patentability mailed May 22, 2012", 6 pgs.
"International Application Serial No. PCT/US2010/057483, International Search Report and Written Opinion mailed Feb. 2, 2011", 7 pgs.
"International Application Serial No. PCT/US2010/057498, International Preliminary Report on Patentability mailed May 22, 2012", 5 pgs.
"International Application Serial No. PCT/US2010/057498, International Search Report mailed Jan. 24, 2011", 2 pgs.
"International Application Serial No. PCT/US2010/057498, Written Opinion mailed Jan. 24, 2011", 4 pgs.
"International Application Serial No. PCT/US2010/057500, International Preliminary Report on Patentability mailed May 31, 2012", 8 pgs.
"International Application Serial No. PCT/US2010/057500, International Search Report mailed Jan. 27, 2011", 2 pgs.
"International Application Serial No. PCT/US2010/057500, Written Opinion mailed Jan. 27, 2011", 6 pgs.
"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.
"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.
"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.
"U.S. Appl. No. 12/950,154, Notice of Allowance mailed Oct. 10, 2014", 6 pgs.
"U.S. Appl. No. 12/950,230, Examiner Interview Summary mailed Nov. 12, 2014", 3 pgs.
"U.S. Appl. No. 12/950,230, Response filed Nov. 2, 2012 to Non Final Office Action mailed Aug. 2, 2012", 8 pgs.
"U.S. Appl. No. 12/950,230, Response filed Nov. 17, 2014 to Non-Final Office Action mailed Jul. 17, 2014", 15 pgs.
"U.S. Appl. No. 12/950,273, Response filed Oct. 24, 2014 to Non-Final Office Action mailed Apr. 25, 2014", 14 pgs.
"U.S. Appl. No. 12/950,355, Notice of Allowance mailed Dec. 9, 2014", 6 pgs.
"U.S. Appl. No. 12/950,355, Response filed Oct. 28, 2014 to Non-Final Office Action mailed Jul. 29, 2014", 21 pgs.
"U.S. Appl. No. 14/143,883, Response filed Dec. 4, 2014 to Non-Final Office Action mailed Aug. 4, 2014", 9 pgs.
"Chinese Application Serial No. 201080052580.9, Office Action mailed Nov. 25, 2014", (W/English Translation), 18 pgs.
"U.S. Appl. No. 12/950,154, Examiner Interview Summary mailed Aug. 19, 2014", 3 pgs.
"U.S. Appl. No. 12/950,154, Response filed Aug. 25, 2014 to Non-Final Office Action mailed Feb. 25, 2014", 18 pgs.
"U.S. Appl. No. 14/454,298, Preliminary Amendment filed Sep. 18, 2014", 7 pgs.
"U.S. Appl. No. 12/950,230, Final Office Action mailed Jan. 13, 2015", 10 pgs.
"U.S. Appl. No. 12/950,230, Non Final Office Action mailed Apr. 15, 2015", 10 pgs.
"U.S. Appl. No. 12/950,230, Response filed Mar. 24, 2015 to Final Office Action mailed Jan. 13, 2015", 11 pgs.
"U.S. Appl. No. 12/950,273, Advisory Action mailed May 12, 2015", 3 pgs.
"U.S. Appl. No. 12/950,273, Final Office Action mailed Feb. 4, 2015", 28 pgs.
"U.S. Appl. No. 12/950,273, Response filed May 4, 2015 to Final Office Action mailed Feb. 4, 2015", 14 pgs.
"U.S. Appl. No. 12/950,273, Response filed Jun. 4, 2015 to Final Office Action mailed Feb. 4, 2015", 14 pgs.
"U.S. Appl. No. 14/109,368, Non Final Office Action mailed Mar. 11, 2015", 6 pgs.
"U.S. Appl. No. 14/109,368, Response filed May 26, 2015 to Non-Final Office Action mailed Mar. 11, 2015", 12 pgs.
"U.S. Appl. No. 14/143,883, Notice of Allowance mailed Jan. 26, 2015", 6 pgs.
"U.S. Appl. No. 14/454,298, Notice of Allowance mailed Mar. 17, 2015", 8 pgs.
"U.S. Appl. No. 14/508,436, Preliminary Amendment filed Jan. 8, 2015", 7 pgs.
"U.S. Appl. No. 14/617,058, Preliminary Amendment filed Feb. 18, 2015", 8 pgs.
"U.S. Appl. No. 14/695,516, Preliminary Amendment filed May 27, 2015", 6 pgs.
"Australian Application Serial No. 2010321745, Office Action mailed Jan. 12, 2015", 3 pgs.
"Australian Application Serial No. 2010321745, Response filed Apr. 24, 2015 to Office Action mailed Jan. 12, 2015", (18 pgs).
"Australian Application Serial No. 2010321812, Office Action mailed Jan. 12, 2015", 3 pgs.
"Australian Application Serial No. 2010321812, Response filed Apr. 24, 2015 to Office Action mailed Jan. 12, 2015", 19 pgs.
"Chinese Application Serial No. 201080052569.2 Response filed Nov. 7, 2014 to Non Final Office Action mailed Jun. 10, 2014", (W/English Translation), 12 pgs.
"Chinese Application Serial No. 201080052569.2, Office Action mailed Jan. 28, 2015", (W/English Translation), 5 pgs.
"Chinese Application Serial No. 201080052569.2, Response filed Mar. 26, 2015 to Office Action mailed Jan. 28, 2015", W/ English Claims, 10 pgs.
"Chinese Application Serial No. 201080052578.1, Office Action mailed Dec. 17, 2014", (W/English Translation), 4 pgs.

(56) References Cited

OTHER PUBLICATIONS

"Chinese Application Serial No. 201080052578.1, Response filed Jan. 22, 2015 to Office Action mailed Dec. 17, 2014", (W/ English Translation), 8 pgs.

"Chinese Application Serial No. 201080052578.1, Response filed Aug. 12, 2014 to Office Action mailed Apr. 1, 2014", W/ English Claims, 13 pgs.

"Chinese Application Serial No. 201080052580.9, Response filed Aug. 14, 2014 to Office Action mailed Apr. 3, 2014", W/ English Claims, 12 pgs.

"Chinese Application Serial No. 201080052583.2, Office Action mailed Dec. 24, 2014", (W/English Translation), 4 pgs.

"Chinese Application Serial No. 201080052583.2, Response filed Sep. 26, 2014 to Office Action mailed Mar. 14, 2014", (W/ English Translation of Claims), 10 pgs.

"U.S. Appl. No. 12/950,230, Notice of Allowance mailed Oct. 7, 2015", 5 pgs.

"U.S. Appl. No. 12/950,230, Response filed Jul. 15, 2015 to Non Final Office Action mailed Apr. 15, 2015", 16 pgs.

"U.S. Appl. No. 12/950,273, Non Final Office Action mailed Nov. 24, 2015", 10 pgs.

"U.S. Appl. No. 14/109,368, Final Office Action mailed Jul. 9, 2015", 10 pgs.

"U.S. Appl. No. 14/109,368, Notice of Allowance mailed Nov. 24, 2015", 10 pgs.

"U.S. Appl. No. 14/109,368, Response filed Nov. 9, 2015 to Final Office Action mailed Jul. 9, 2015", 17 pgs.

"U.S. Appl. No. 14/454,298, Notice of Allowance mailed Jul. 1, 2015", 6 pgs.

"U.S. Appl. No. 14/508,436, Non Final Office Action mailed Sep. 11, 2015", 7 pgs.

"U.S. Appl. No. 14/508,436, Response filed Dec. 11, 2015 to Non Final Office Action mailed Sep. 11, 2015", 10 pgs.

"U.S. Appl. No. 14/724,160, Non Final Office Action mailed Sep. 11, 2015", 5 pgs.

"U.S. Appl. No. 14/724,160, Preliminary Amendment filed Jun. 17, 2015", 8 pgs.

"U.S. Appl. No. 14/724,160, Response filed Nov. 25, 2015 to Non Final Office Action mailed Sep. 11, 2015", 8 pgs.

\* cited by examiner

METHOD FOR SUBCHONDRAL TREATMENT OF JOINT PAIN USING IMPLANTABLE DEVICES

CROSS REFERENCE TO RELATED APPLICATIONS

This application is a continuation of U.S. patent application Ser. No. 12/950,183 filed on Nov. 19, 2010, which claims priority to U.S. Provisional No. 61/354,100 filed Jun. 11, 2010, and entitled "IMPLANTABLE DEVICES AND RELATED DELIVERY TOOLS, " and U.S. Provisional No. 61/263,170 filed Nov. 20, 2009, and entitled "METHOD FOR TREATING JOINT PAIN AND ASSOCIATED INSTRUMENTS," which are herein incorporated by reference in their entirety.

This application also related to co-pending and co-owned U.S. patent application Ser. No. 12/950,355, filed Nov. 19, 2010 and entitled "SUBCHONDRAL TREATMENT OF JOINT PAIN, " the content of which is herein incorporated in its entirety be reference.

FIELD

The present invention relates to devices for the surgical treatment of bone tissue, and more particularly to implantable devices and related delivery tools for the surgical repair or treatment of damaged bone tissue, especially at or near a joint. Even more particularly, the implantable device can be formed from a bone material.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

Yet, even now there still remains a concern with the introduction of an implantable device made of foreign materials (i.e., metals, polymers or combinations of both) into the human body. And although there exists a number of biocompatible metals and polymers currently considered acceptable for short to long-term placement within a patient, there continues to be questions associated with the interaction between the medical device and the tissues and physiological systems of the patient. Moreover, in cases where the implantable device is being placed into a dynamic environment such as in or near a bone joint, where different forces are acting upon the area to be treated, the biomechanical risks of introducing a material having different physical properties than naturally occurring bone are still unknown. What is known, however, is that the implantable device should mimic as close as possible to naturally occurring bone in both its biomechanical and physiological functions as well as its biological properties.

Accordingly, it is desirable to provide implantable devices that can provide mechanical strength and structural integrity to the area to be treated, while also being as physiologically and biologically compatible as possible to reduce or eliminate any potential negative effects to the patient. It would also be beneficial to provide such devices having the ability to facilitate the dispersal of hardening or augmentation material in the same area. It is further desirable to provide implantable devices that are configured for the treatment or repair of damaged bone tissue particularly at the joints, and even more particularly at the subchondral bone level.

SUMMARY

The present disclosure provides implantable devices formed of bone material for placement inside bone. The devices are configured to provide mechanical strength and structural integrity to bone tissue to be treated, while also being physiologically and biologically compatible. In addition, the devices facilitate the dispersal of hardening or augmentation material in the same area. These implantable devices are configured for the treatment or repair of damaged bone tissue at the joints, and even more particularly at the subchondral bone level. Also provided are delivery tools for delivering the devices to the area of bone to be treated.

In one exemplary embodiment, an implantable device for treatment of a bone defect is disclosed. The device may include a first, leading end, a second, trailing end, and a main body extending between the ends. A central opening may extend through the length of the main body, and a channel may be provided in fluid communication with the central opening to allow extrusion of a flowable material from the central opening to outside the main body. The device may be formed of bone material, such as allograft material.

In another exemplary embodiment, a method of treating a bone defect is provided. The method comprises the steps of providing an implantable device having a first, leading end, a second, trailing end, and a main body extending between the ends, a central opening extending through the length of the main body, and a channel in fluid communication with the central opening to allow extrusion of a flowable material from the central opening to outside the main body, the device being formed of allograft material. The implantable device may be implanted adjacent the bone defect. A flowable material may be introduced through the central opening and out of the channel. The flowable material may be allowed to extrude away from the device.

In another exemplary embodiment, an implantable device for treatment of a bone defect is disclosed. The device may include a first, leading end, a second, trailing end, and a main body extending between the ends. The main body may comprise at least one recess extending down at least a portion of the main body. The device may be formed of a bone material, such as an allograft material.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
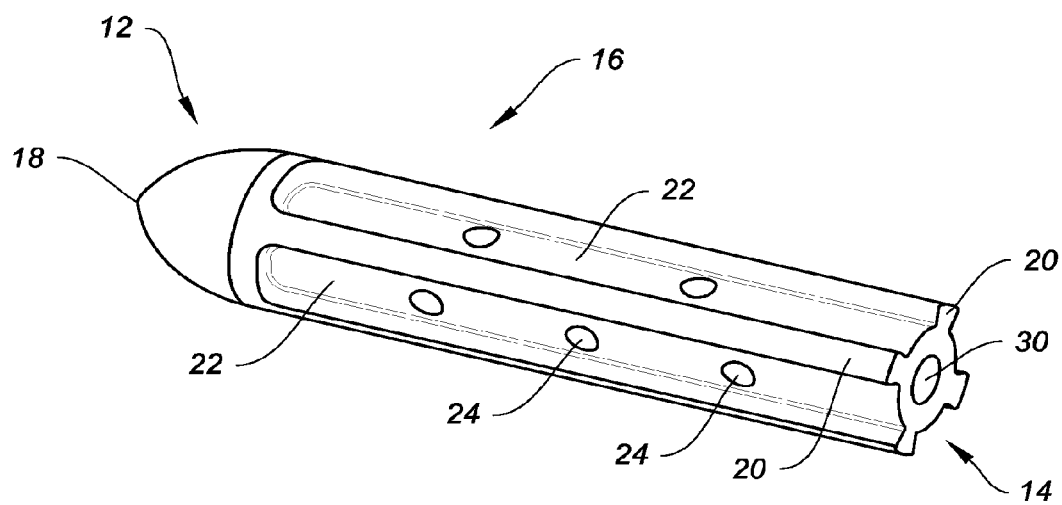
FIG. 1 is a perspective view of an exemplary embodiment of an implantable device of the present invention.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure. This procedure and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface or periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatments can be administered on acute stress fractures, BML or BME, or other subchondral defects, as previously mentioned.

According to the embodiments, the SCP™ treatment may continue after surgery. In particular, the patient may be monitored for a change in pain scores, or positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, and associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity. In addition, some of the soft bone tissue may be compacted prior to insertion of the material.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis. In addition, some of the soft bone tissue may be compacted in order to aid in stimulation.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implant may be placed in cancellous bone, through sclerotic bone, or under sclerotic bone at the affected bone region. In order to create a void or space for the implant, some of the soft bone tissue at or near the bone marrow lesion or defect may be compacted. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument. Exemplary guide instruments, navigation, and targeting systems are also disclosed in co-pending and co-owned U.S. patent application Ser. No. 12/950,230, filed Nov. 19, 2010 and entitled "INSTRUMENTS FOR TARGETING A JOINT DEFECT," U.S. Patent Application No. 12/950,154, filed Nov. 19, 2010 and entitled "INSTRUMENTS FOR VARIABLE ANGLE APPROACH TO A JOINT," U.S. patent application Ser. No. 12/950,114, filed Nov. 19, 2010and entitled "COORDINATE MAPPING SYSTEM FOR JOINT TREATMENT," U.S. patent application Ser. No. 12/950,061, filed Nov. 19, 2010 and entitled "NAVIGATION AND POSITIONING INSTRUMENTS FOR JOINT REPAIR," the contents of which are herein incorporated in their entirety by reference.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be used in combination with cements or hardening materials commonly used to repair damaged bone by their introduction into or near the site of damage, either to create a binding agent, cellular scaffold or mechanical scaffold for immobilization, regeneration or remodeling of the bone tissue.

In general, the embodiments relate to implantable devices for the surgical treatment of bone, and particularly to a bone defect at a joint region, and even more particularly at the subchondral bone level of the joint region. Provided are implantable devices made of bone material for improved physiological and biological compatibility. The devices are configured to provide mechanical strength and structural integrity to bone tissue to be treated, while also being physiologically and biologically compatible. In addition, the devices facilitate the dispersal of a flowable material such as a hardening or augmentation material in the same area.

The present disclosure provides suitable implantable fixation devices for the surgical treatment of these altered bone regions or bone defects, especially at the subchondral level. These implantable devices are configured to provide mechanical strength and structural integrity to bone tissue to be treated, while also facilitating the dispersal of hardening or augmentation material in the same area. In addition, these implantable devices are formed of bone material, such as allograft material, thereby making them physiologically and biologically compatible as well as biomechanically similar to naturally occurring bone.

Turning now to the drawings, implantable devices particularly suitable for implantation in certain areas of the bone, such as near the periarticular surface or the subchondral bone area (usually within the range of about 2-15 mm from the bone's articular surface) are shown. FIG. 1 illustrates an exemplary embodiment of an implantable device of the present disclosure. Implantable device 10 can include a main body 16 extending between a first, leading end 12 and a second, trailing end 14. The first, leading end 12 of the implantable device 10 can include a tapered nose or tip 18 to facilitate ease of insertion to the target site. If so desired, however, the tip 18 may also be rounded or it may be flattened.

In addition, a surface feature may be present on the main body 16 for enhanced bone tissue engagement with the target site. In the embodiment shown, the surface feature may comprise a rib or fin 20. One or more fins 20 can be provided in the present embodiment. The fins 20 may help to facilitate a press-fit connection of the implantable device 10 to the insertion site or cavity. The fins 20 of FIG. 1 may have a uniform height across their length, or the fins 20 may have varying heights across their length to create a curved, wavy, or irregular pattern. For example, the fins 20 may be S-shaped, V or W-shaped to create a jagged spine-like profile along the length of the main body 16. It is contemplated that the surface feature may also include structural elements such as threads, teeth, barbs, bumps, spikes, or other surface enhancements. These surface enhancements may serve as anti-migration features after implantation.

As previously mentioned, the implantable device 10 may further be augmented with a flowable material, such as a bone cement or augmentation material like a bone void filler as previously described, other biological agent, or an osteoconductive, osteoinductive and/or osteogenic agent like a bone graft material. The flowable material may be introduced through the implantable device, around the implantable device, and/or apart from the implantable device but at the affected bone region, such as into the lower region of a defect like a bone marrow lesion. For example, the implantable device 10 may act as a portal for injecting the flowable material into the defect area, where the defect area could be in the subchondral bone region.

As shown, the main body 16 may include one or more recesses or flutes 22 extending along the longitudinal axis of the implantable device 10. The flutes 22 are flattened, depressed regions of the main body 16 and separate the fins 20 around the circumference of the main body 16. The implantable device 10 may be cannulated and provided with a central canal or opening 30, as shown. The central opening 30 may have a threaded end 40 (see FIGS. 4A-4C) for attachment to a delivery tool or injection system. Further the implantable device 10 may be fenestrated, with one or more pores or channels 24 provided on the flutes 22, with each pore or channel 24 being in fluid communication with the central opening 30 of the implantable device 10. The channels 24 enable the user to introduce a flowable material, such as a bone cement or augmentation material as previously described, into the central opening 30 and allow the material to extrude out of the channels 24 and into the recesses or flutes 22. The central opening 30 would enable the flowable material to be introduced through the implantable device 10, while the channels 24 would allow the material to be ejected around the implantable device 10. The flutes 22 around the main body 16 create voids or open space around the implantable device 10 to accommodate the flowable material. The pores or channels 24 can also provide access for bone ingrowth and vasculature permeation.

Although shown with a plurality of channels 24, each being similar in size, it is understood that the dimensions of the channels 24 may vary. For example, it is contemplated that the channels 24 may have incremental sizes along the length of the main body 16. Also, the channels 24 may have a predetermined spatial pattern, such as for example, a staggered arrangement, instead of being coaxial. Further, in another exemplary embodiment the implantable device 10 can include channels 24 in only one section of the main body 16, thereby imparting directional control and enabling augmentation material to be extruded in only that area of the implantable device 10. For instance, in one embodiment the channels 24 may be isolated to the lower portion of the main body 16 and be provided in only the lower half of each of the flutes 22. In another embodiment, channels 24 may be provided on only one of the flutes 22. By selectively providing channels 24 in a discrete portion of the implantable device 10, the user is able to control the direction in which the flowable material is extruded.

While the main body 16 is shown as being substantially cylindrical, it is understood that the main body 16 may be shaped so as to have varying diameters along its length. For instance, the main body 16 may have a figure "8" shape, a bowling pin shape, a U-shape, a crescent or C-shape, an I-beam shape, a rectangular or square shape, a star shape, or corkscrew shape, etc. so long as it is suitable for insertion into bone tissue and has enough structural integrity to perform its intended function of bridging a fracture or fissure, supporting bone regrowth or remodeling, and/or binding the bone tissue together to prevent further breakdown or degeneration. The implantable device 10 may be formed of a bone material such as allograft or cadaver bone, including cortical, cortico-cancellous, bi-cortical, tri-cortical, or sesamoid bone material. The bone material allows for improved physiological and biological compatibility, since it mimics the patient's natural bone tissue. In addition, radiopaque markers may be employed with the implantable device 10 for imaging possibilities.

However, while bone material provides certain desirable benefits to the implantable device 10 as previously mentioned, a bone implant can also be relatively weak and brittle, and present challenges in its delivery and ultimate placement, particularly inside bone tissue. As described in the exemplary embodiment above, the cannulated and fenestrated allograft device 10 could be very fragile and break during insertion before the device 10 can be supported by a hardening material like cement. To overcome this obstacle, various insertion and delivery tools for use with the implantable device 10 of the present disclosure are also provided.

Figure 2A:
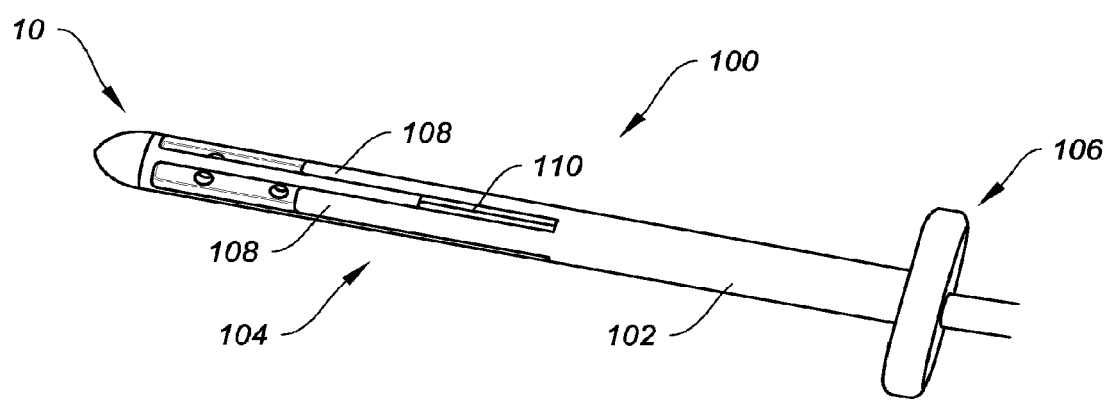
FIG. 2A is a perspective view of the device of FIG. 1 with an exemplary embodiment of an insertion tool of the present invention.
Figure 2B:
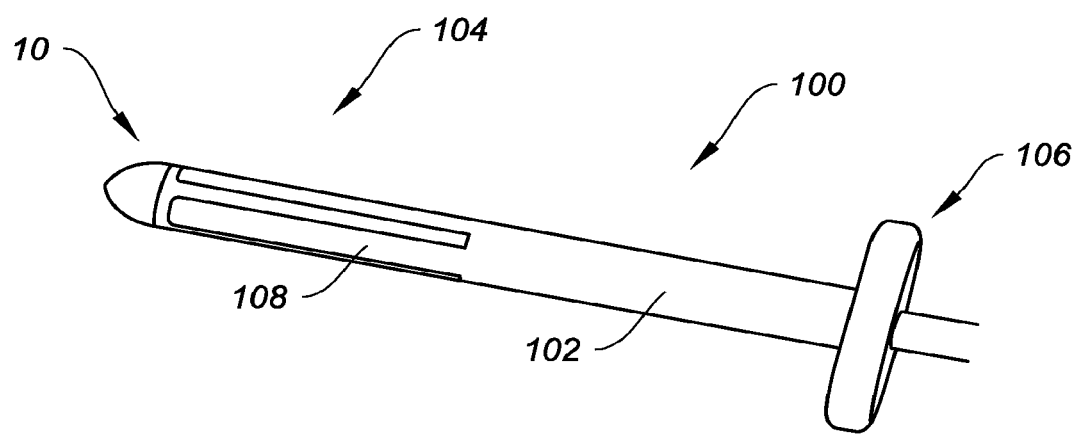
FIG. 2B shows the device and the associated insertion tool of FIG. 2A fully engaged.
Figure 2C:
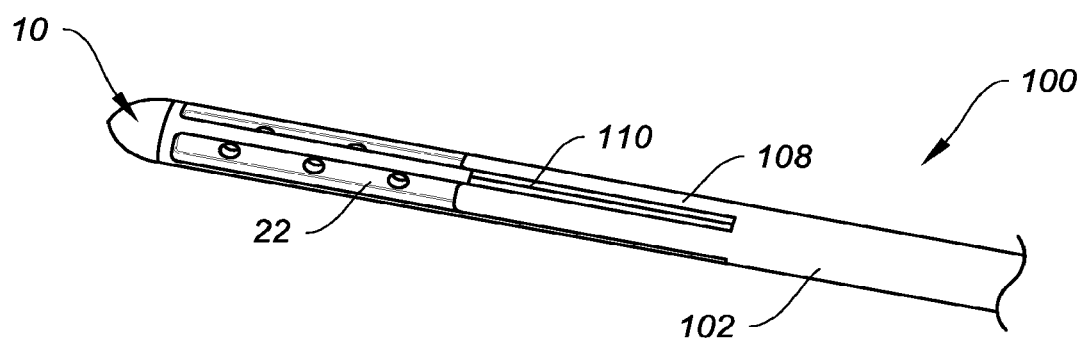
FIG. 2C shows the device and the associated insertion tool of FIG. 2A partially disengaged.

FIGS. 2A-2C illustrate one exemplary embodiment of a tool of the present disclosure. As shown, inserter tool 100 may include a shaft 102 having at one end a device-engaging portion 104 and at an opposite end a handle portion 106. The device-engaging portion 104 may comprise finger-like projections 108 extending out from the shaft 102 and separated by slots 110 in between. The finger-like projections 108 may be configured to slide along, and reside inside the recesses 22 of the implantable device 10, thereby allowing the inserter tool 100 to firmly support or grip the implantable device 10 but without significantly increasing the overall outer diameter of the device 10. It is contemplated that each of the projections 108 can be independently operational, such that the user may be able to manipulate a projection 108 separately and independent of the other projections 108.

FIG. 2A shows the inserter tool 100 with its projections 108 extending inside about halfway down the length of the flutes 22 of the implantable device 10, whereas FIG. 2B shows the inserter tool 100 fully engaged with the implantable device 10. In this scenario, the projections 108 cover the entire length of the flutes 22 and provide the maximum protection to the implantable device 10 during implantation. In contrast, FIG. 2C shows the inserter tool 100 retracted from the implantable device 10 and with the projections 108 disengaged from the implantable device 10, such as near the end of the implantation process. In this scenario, the projections 108 can be slid out of the flutes 22 and the inserter tool 100 slightly rotated so that the projections 108 are no longer aligned with the flutes 22. Accordingly, during the delivery process the implantable device 10 may be entirely supported within the device-engaging portion 104 of the inserter tool 100 until the projections 108 are retracted and the device 10 is released from the inserter tool 100 to its desired location.

Figure 3A:
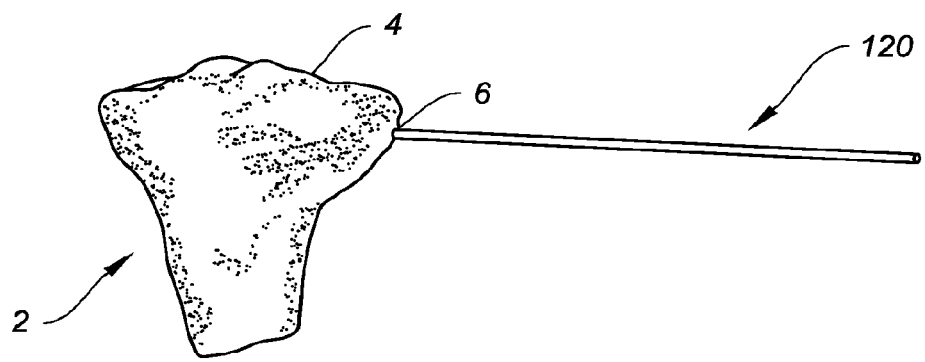
FIGS. 3A-3Q illustrate an exemplary method of delivering the implantable device of FIG. 1 into a bone.
Figure 3B:
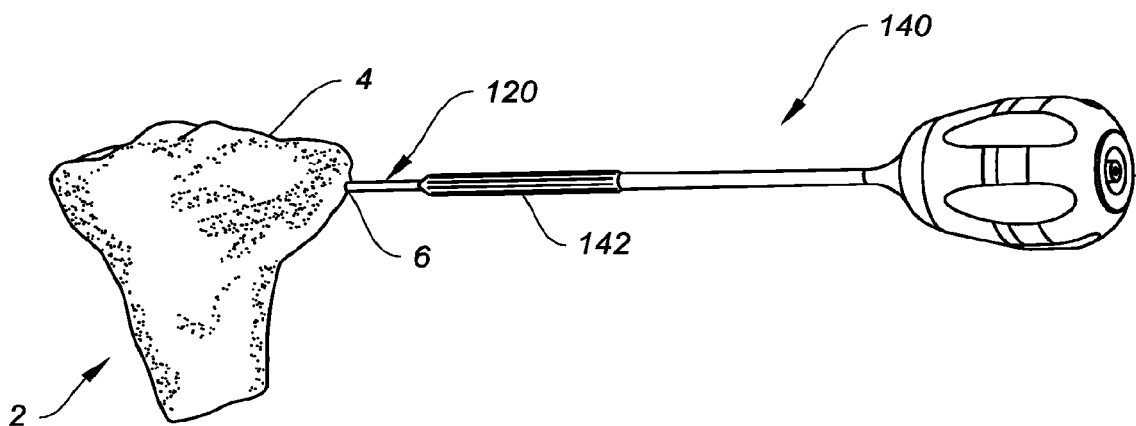
Figure 3C:
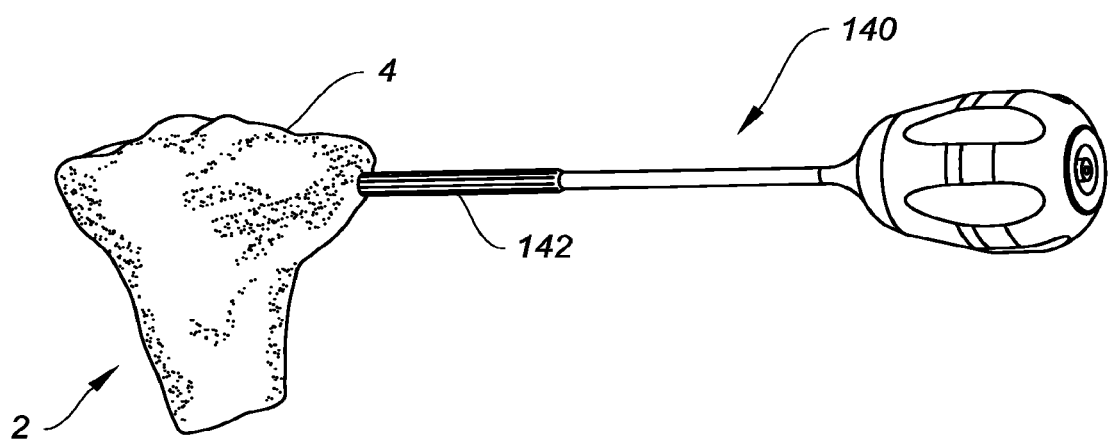
Figure 3D:
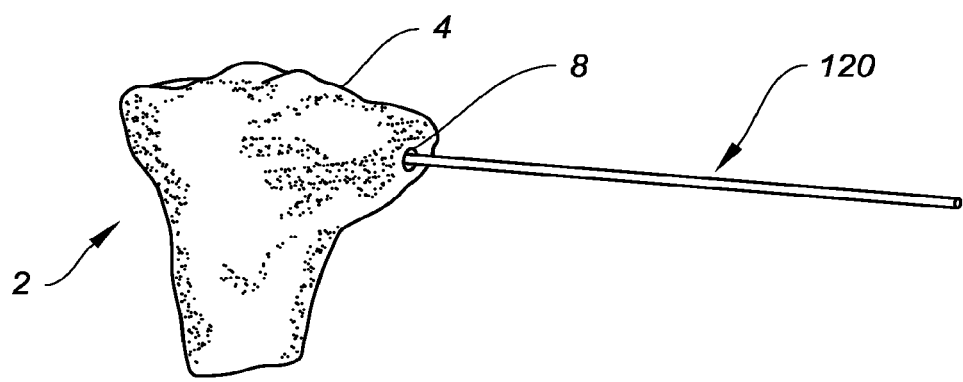
Figure 3E:
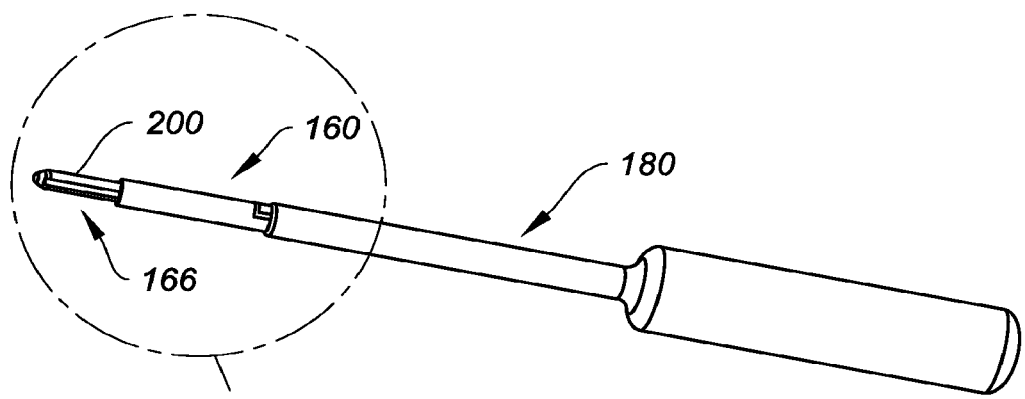
Figure 3F:
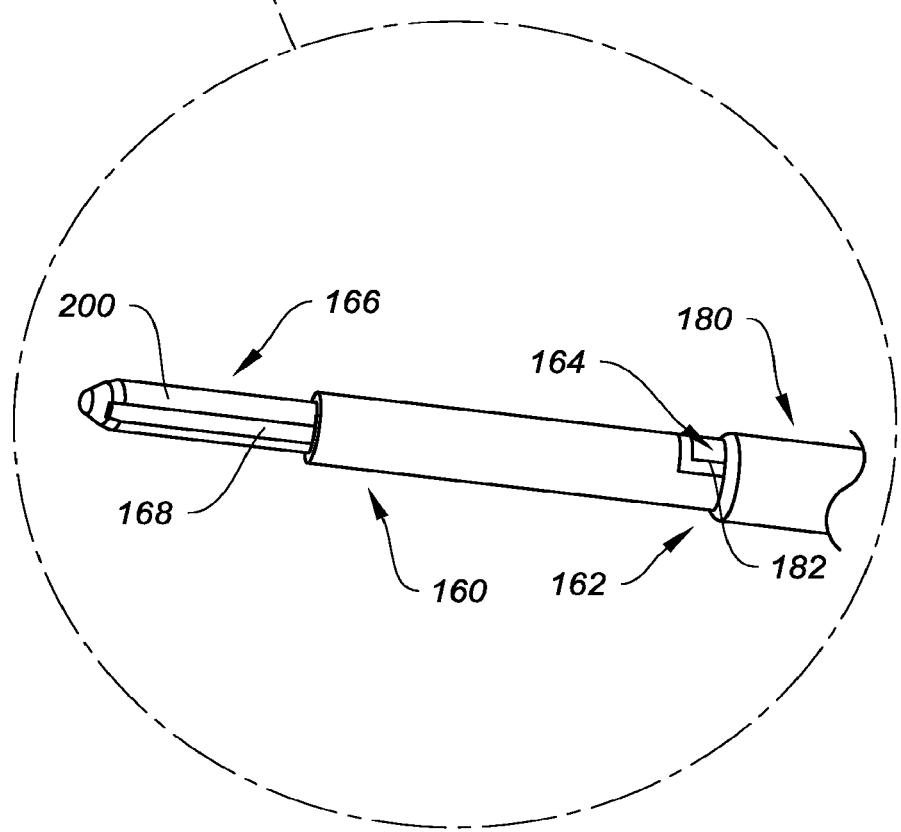
Figure 3G:
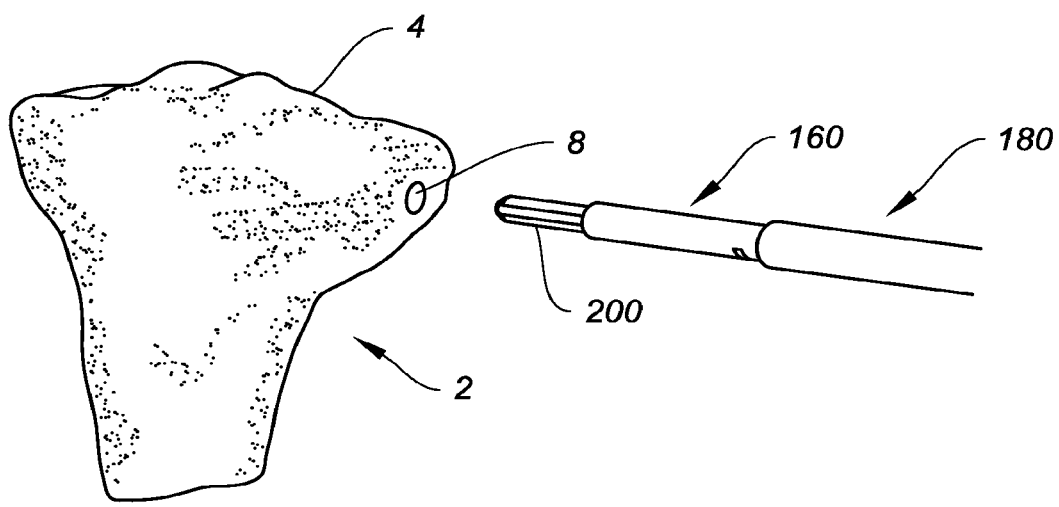
Figure 3H:
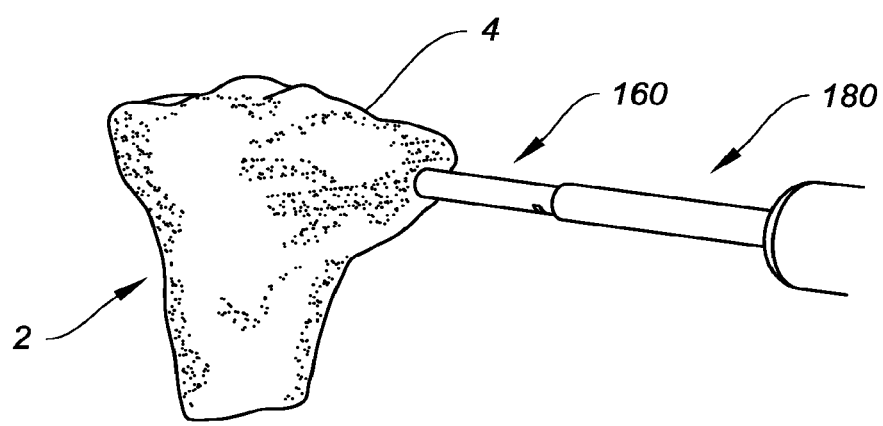
Figure 3I:
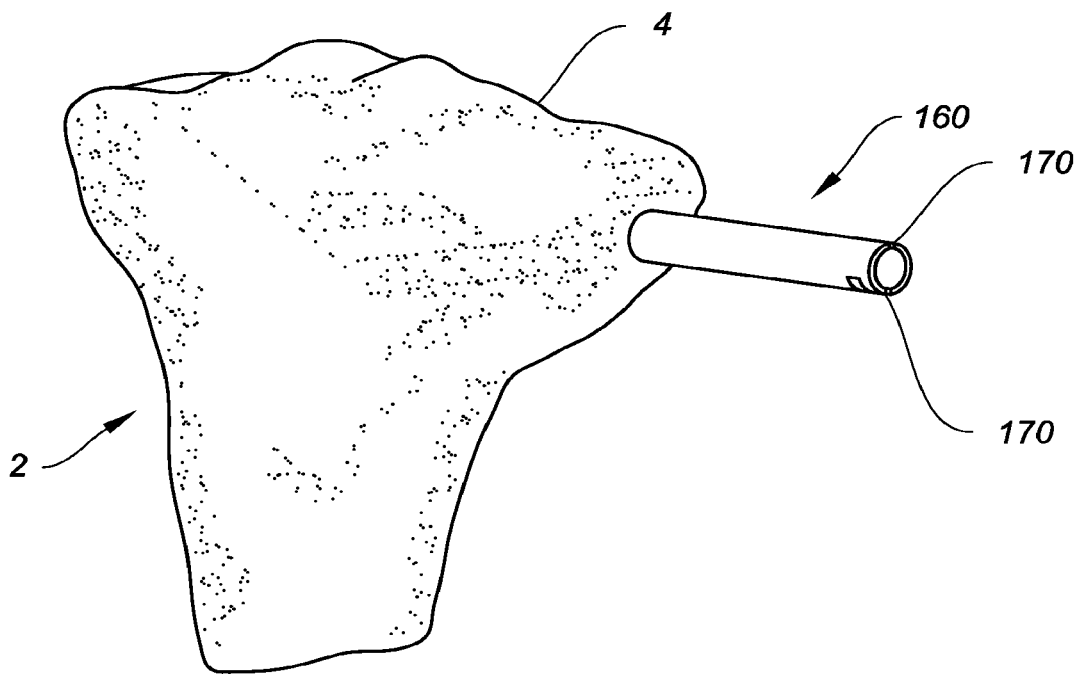
Figure 3J:
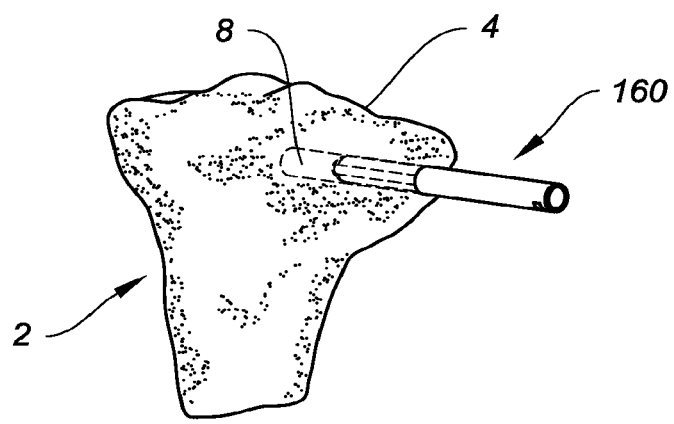
Figure 3K:
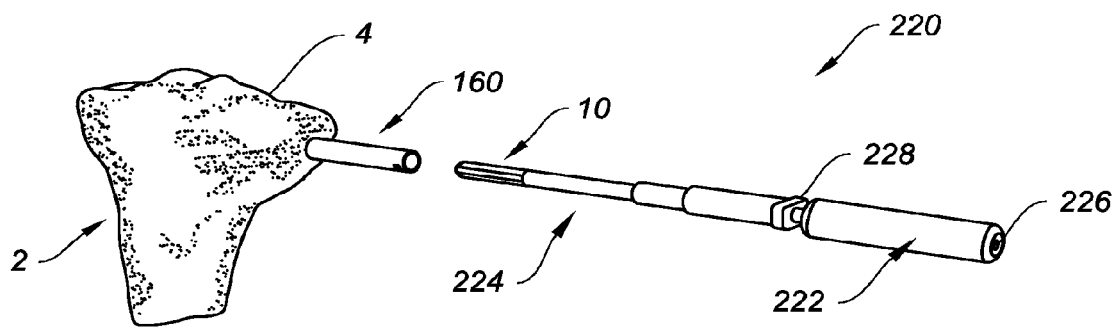
Figure 3L:
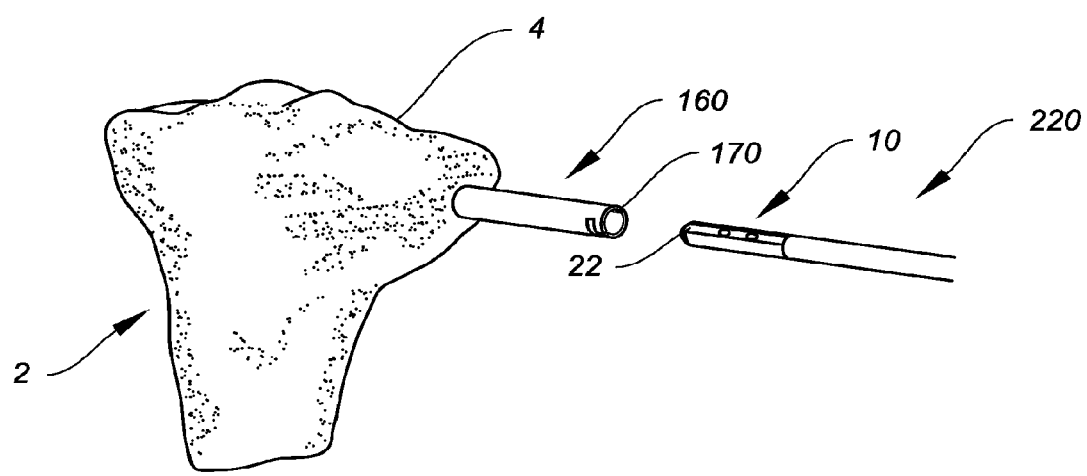
Figure 3M:
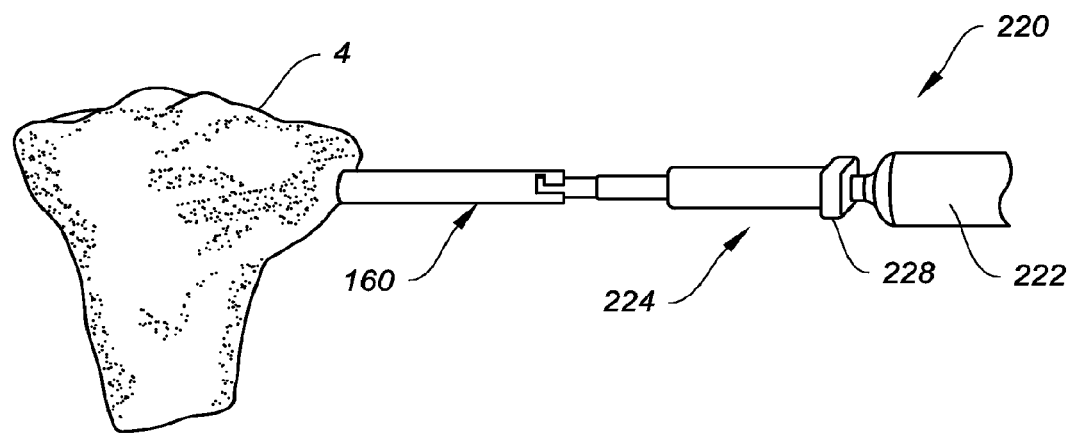
Figure 3N:
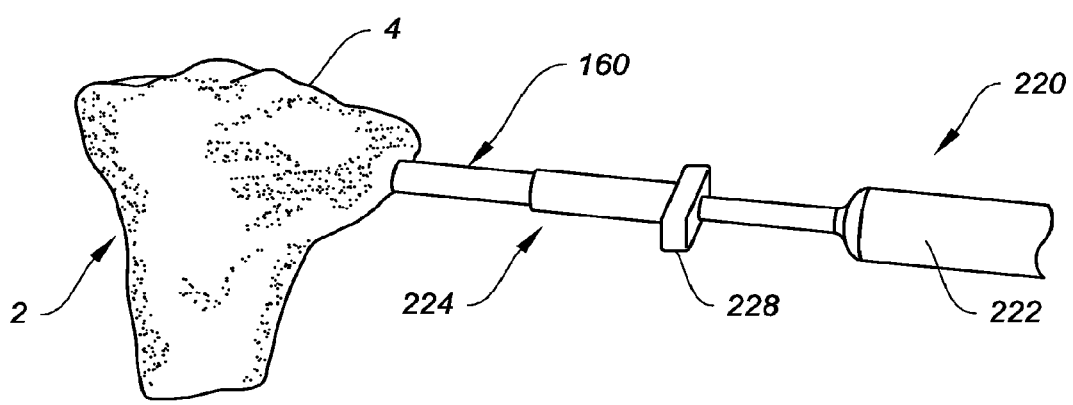
Figure 3O:
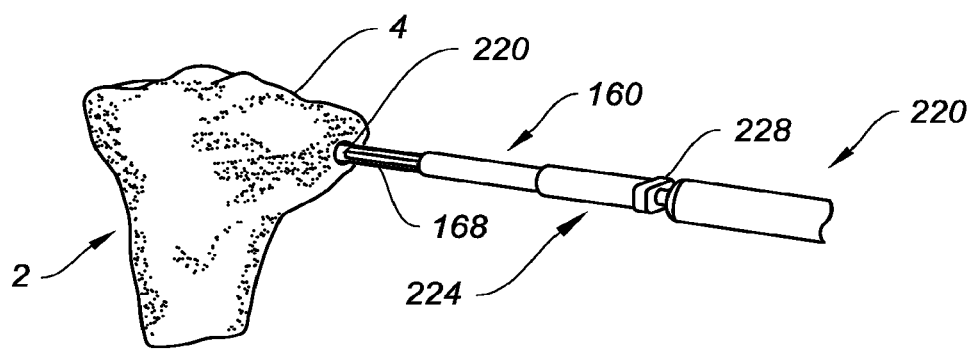
Figure 3P:
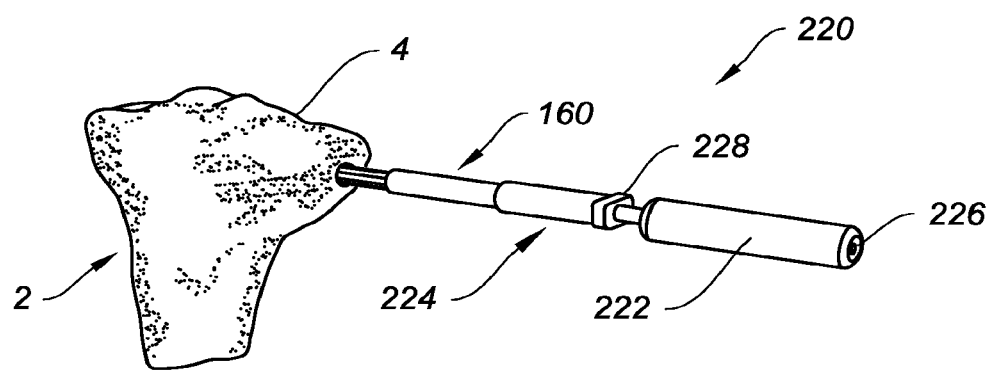
Figure 3Q:
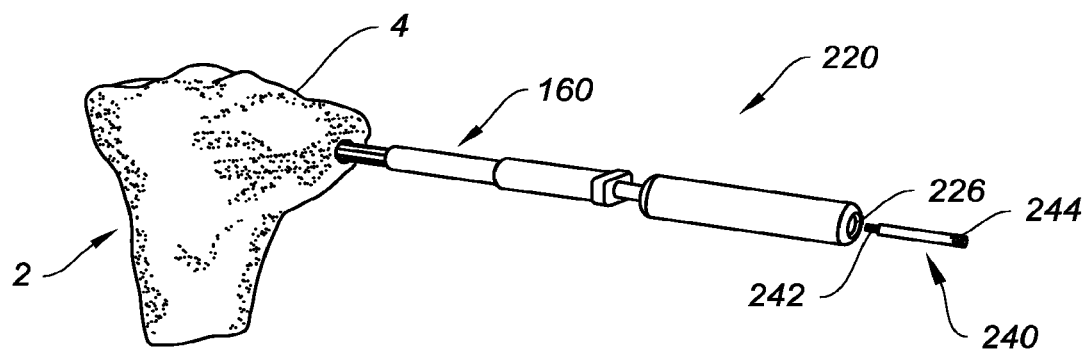

FIGS. 3A-3Q illustrate one exemplary method of using the implantable device 10 and other exemplary embodiments of insertion and delivery tools of the present disclosure, in which the implantable device 10 may be used to treat a bone defect in a bone 2 of a joint. As shown, the bone 2 may be a tibia of a knee joint, while the defect may be a bone marrow lesion at the subchondral level below the articular surface 4. FIG. 3A shows a guidewire or pin 120 placed at the target area 6 of the bone 2 to be treated. FIG. 3B shows a cannulated reamer 140 slid over the pin 120. The cannulated reamer 140 may be provided with a shaped cutting portion 142 for boring a cavity or hole 8 in the bone 2 for receiving the implantable device 10, as further shown in FIG. 3C. The shaped cutting portion 142 may have a geometry matching that of the implantable device 10. The cannulated reamer 140 may be operated manually or it may be powered. After a sufficiently sized hole 8 has been prepared, the cannulated reamer 140 may be removed, as illustrated in FIG. 3D, and then the pin 120 can next be removed. In addition, it has been discovered that the bone tissue surrounding a bone marrow lesion tends to be relative soft (usually, edema is present) compared with normal, healthy bone tissue. Accordingly, the surgeon may also compact some of the soft bone tissue and then optionally insert an implant, such as implantable device 10, into the area adjacent to the compacted bone tissue.

FIGS. 3E and 3F show exemplary embodiments of other inserter tools including a delivery tube 160, delivery tool 180 and obturator 200. The delivery tube 160 may include a slot 164 at a tool-engaging end 162 for releasable engagement with a notch 182 on the delivery tool 180. Of course, other mechanisms for attachment and quick release may be employed as is known in the art. At the opposite end of the delivery tube 160 extend guide fingers 168 that form the device-engaging portion 166 of the delivery tube 160. These guide fingers 168 function in the same manner as the projections 108 of inserter tool 100, and are able to slide in and out of the flutes 22 of the implantable device 10.

As further shown, an obturator 200 is provided having the same size and shape as the implantable device 10 to be delivered. The obturator 200 is intended as a metal or polymeric replica of the implantable device 10, and can be used to expand the cavity 8 or confirm that there is adequate room to receive the implantable device 10. In addition, the obturator 200 facilitates positioning of the delivery tube 160, as will be shown later. The obturator 200 may be held by the guide fingers 168 of the delivery tube 160, as illustrated.

Turning now to FIGS. 3G and 3H, the delivery tube 160, delivery tool 180 and attached obturator 200 can be assembled together, and the delivery tube 160 with the obturator 200 can be placed completely into the bored hole 8 previously created. The delivery tube 160 is properly positioned when the obturator 200 is in the same position as desired for the implantable device 10. Although not shown, it is contemplated that the delivery tube 160 may have surface features such as teeth or barbs to anchor it to the bone 2.

Once the delivery tube 160 has been properly positioned and anchored to the bone 2, the obturator 200 and the delivery tool 180 may be removed, leaving just the delivery tube behind, as illustrated in FIG. 3I. This removal step could be achieved by simply pulling the delivery tool 180 (which is also attached to the obturator 200) straight out from the delivery tube 160 and releasing the slot 164 of the delivery tube 160 from the notch 182 of the delivery tool. As the partial cross-sectional view of FIG. 3J depicts, the guide fingers 168 of the delivery tube 160 remain positioned against the cavity 8 created in the bone 2. The delivery tube 160 itself provides a working channel through which the implantable device 10 may be inserted into the cavity 8, and prevents collapse of the implantable device 10 during the process. In addition to supporting the implantable device 10, the delivery tube 160 prevents or controls flow of any injected flowable materials through the implantable device 10.

FIGS. 3K and 3L illustrate the implantable device 10 of the present disclosure attached to a device insertion tool 220. The device insertion tool 220 may be cannulated, and comprise a main channel 222 onto which is a telescoping channel 224. The telescoping channel 224 includes a grip 228 for manipulating the telescoping channel relative to the main channel 222. Although not shown, it is contemplated that the implantable device 10 may be threadedly attached to the device insertion tool 220 at the distal end of the main channel 222. Using the device insertion tool 220, the implantable device 10 is aligned with the delivery tube 160. As was shown in FIG. 3I, the delivery tube 160 includes internal ribs 170 that act as guide rails for insertion of the implantable device 10 therethrough. Accordingly, the flutes 22 of the implantable device 10 can be mated to the internal ribs 170 of the delivery tube 160 to align the device 10 for proper insertion.

Upon proper placement of the implantable device 10 inside the cavity 8, a flowable material such as cement may then be injected into the implantable device 10 to strengthen the entire construct. The telescoping channel 224 of the device insertion tool 220 may be slid down and engaged with delivery tube 160 so that the delivery tube 160 is locked to the telescoping channel 24, as shown in FIGS. 3M and 3N. Then, the grip 228 of the device insertion tool 220 may be pulled back, as shown in FIGS. 3O and 3P, to cause retraction of the delivery tube 160 and guide fingers 168 from the bone 2. It is contemplated, of course, that the device delivery tool 220 could also allow modular movement of the guide fingers 168, such that the guide fingers 168 could be retracted in sync or independent of one another as desired to control the flow of material out of the implantable device 10. That is, the channels 24 of the implantable device 10 may be selectively uncovered to allow extrusion of cement from only those uncovered channels 24.

In one embodiment, an injection port 240 may be provided with a Luerlok-type configuration for attaching the device delivery tool 220 to the flowable material injection system. As shown in FIG. 3Q, the device delivery tool 220 may include a threaded opening 226 for receiving a threaded end 242 of the injection port 240. The opposite or injection connecting end 244 of the injection port 240 may be configured like a Luer port, for instance, to connect to the flowable material injection system. The steps of retracting the guide fingers 168 and the injection of flowable material may be done simultaneously, or step-wise in a controlled manner.

Additionally, a slap hammer (not shown) may be provided to remove the delivery tube 160 completely from the bone 2 at the end of the procedure. Further a custom tamp (not shown) may be provided for proper impaction of the implantable device 10 into the bone cavity 8. The tamp could also be provided with an internal recess or cavity that may contain an injection port. It is contemplated that the tamp could be configured with the dual purpose of serving as a slaphammer as well, by allowing the user to control the direction of force to be applied with the instrument. Either one of these additional features may be integrated into the device delivery tool 220.

Figure 4A:
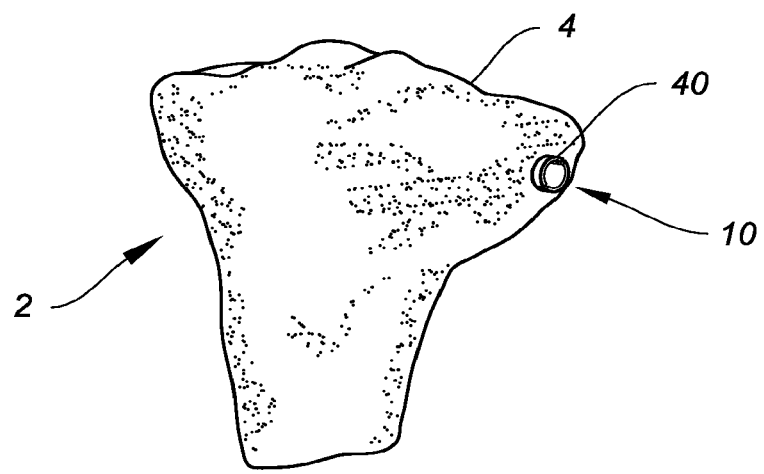
FIGS. 4A-4C illustrate another exemplary method of delivering a flowable material into the implantable device of FIG. 1 into a bone.
Figure 4B:
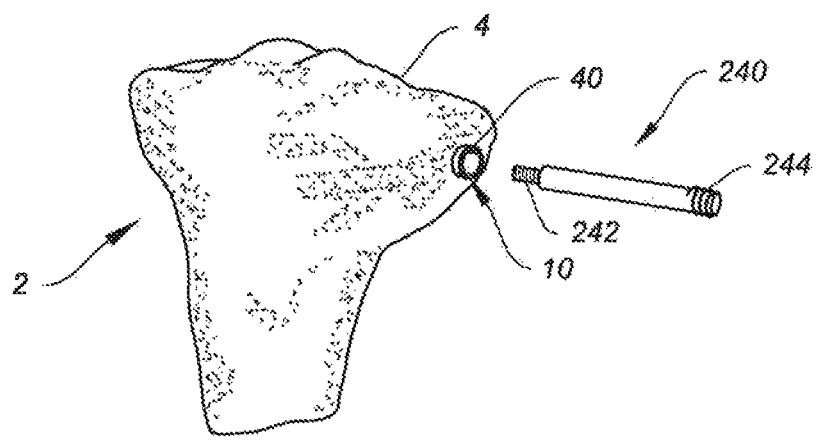
Figure 4C:
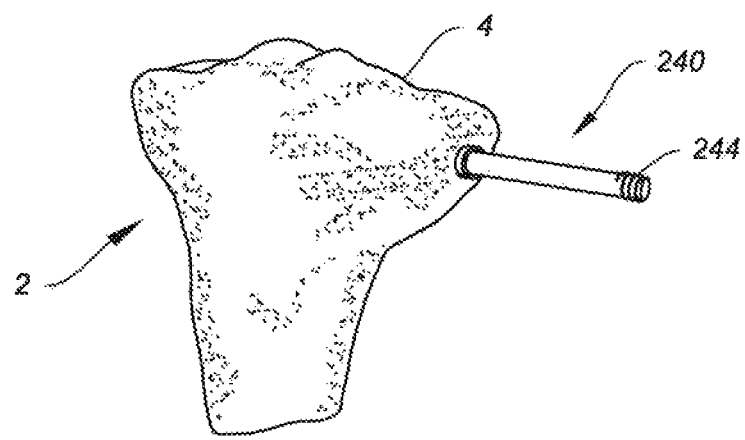

FIGS. 4A-4C illustrate another exemplary embodiment of a method of using the implantable device 10 of the present disclosure. In this method, the injection port 240 would be directly attached to the implantable device 10, and make the implantable device 10 ready for cement injection. As shown in FIGS. 4B and 4C, the threaded end 242 of the injection port 240 could be threadedly attached to the implantable device 10 and allow a more direct connection between the cement injector and the implantable device 10. It should be noted that, while FIGS. 4A-4C show the second, trailing end 14 of the implantable device 10 exposed and outside of the bone 2, the implantable device 10 is intended to be positioned within the cavity 8. The depictions of the implantable device 10 extending beyond the bone 2 is purely for the illustrative purpose of showing the connection between the implantable device 10 and the injection port 240 only.

The implantable devices 10 of the present disclosure may be used to repair bone defects in a joint region such as the knee, shoulder, ankle, hip or other joint of the patient's body. The implantable devices may be useful, for example, in repairing an insufficiency fracture of a bone at a joint.

While the implantable devices 10 have been described as being used with an injectable or flowable material, it is understood, however, that these implants shown and described herein may be used alone without any injectable or flowable material if so desired.

Figure 5A:
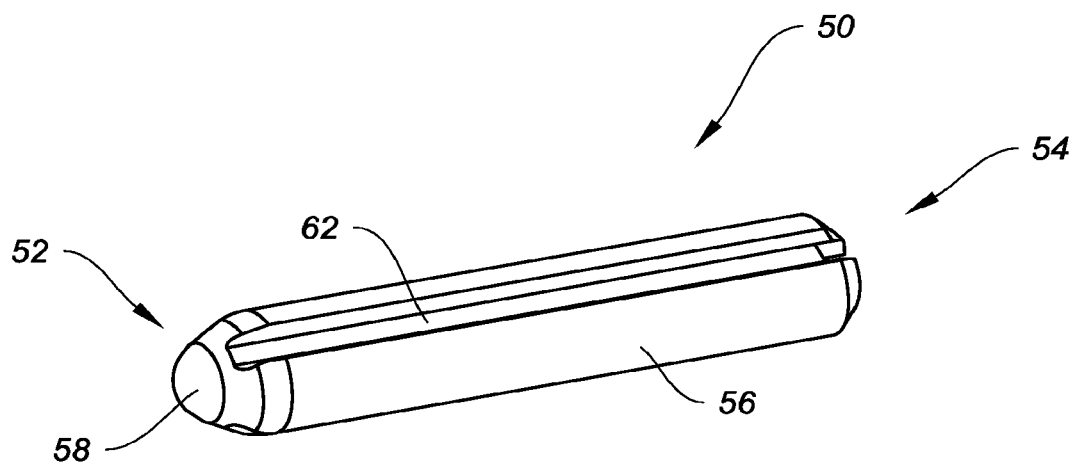
FIGS. 5A-5B illustrate another exemplary embodiment of an implantable device of the present invention.
Figure 5B:
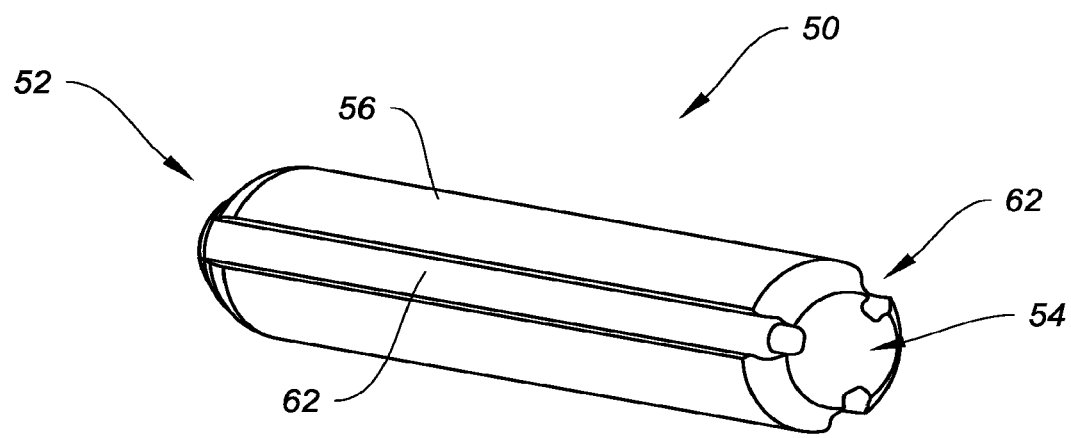

FIGS. 5A-5B illustrate another exemplary embodiment of an implantable device. As shown, the implantable device 50 may have similarities to the implantable device 10 described above. Implantable device 50 can include a main body 56 extending between a first, leading end 52 and a second, trailing end 54. The first, leading end 52 of the implantable device 50 can include a tapered nose or tip 58 to facilitate ease of insertion to the target site. If so desired, however, the tip 58 may also be rounded or it may be flattened. In addition, a surface feature may be present on the main body 56 for enhanced bone tissue engagement with the target site.

Like implantable device 10, the implantable device 50 may further be augmented with a flowable material, such as a hardening material like a bone cement or augmentation material, such as a bone void filler, as previously described, other biological agent, or an osteoconductive, osteoinductive and/or osteogenic agent like a bone graft material. The flowable material may be introduced around the implantable device, and/or apart from the implantable device but at the affected bone region, such as into the lower region of a defect like a bone marrow lesion.

As shown, the main body 56 can be substantially solid and may include one or more recesses or flutes 62 extending along the longitudinal axis of the implantable device 50. The flutes 62 are depressed regions of the main body 56. The recesses 62 allow flowable material to be contained around the periphery of the device 50.

While the main body 56 is shown as being substantially cylindrical, it is understood that the main body 56 may be shaped so as to have varying diameters along its length. For instance, the main body 56 may have a figure "8" shape, a bowling pin shape, a U-shape, a crescent or C-shape, an I-beam shape, a rectangular or square shape, a star shape, or corkscrew shape, etc. so long as it is suitable for insertion into bone tissue and has enough structural integrity to perform its intended function of bridging a fracture or fissure, supporting bone regrowth or remodeling, and/or binding the bone tissue together to prevent further breakdown or degeneration.

Like implantable device 10, the implantable device 50 may be formed of a bone material such as allograft or cadaver bone, including cortical, cortico-cancellous, bi-cortical, tri-cortical, or sesamoid bone material. The allograft material allows for improved physiological and biological compatibility, since it mimics the patient's natural bone tissue.

Figure 6A:
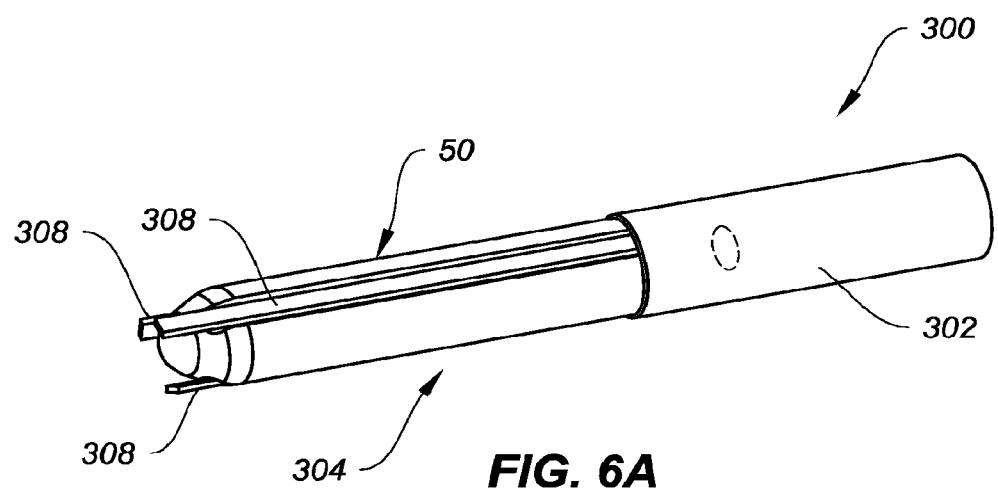
FIG. 6A shows an inserter tool with the device of FIGS. 5A and 5B.
Figure 6B:
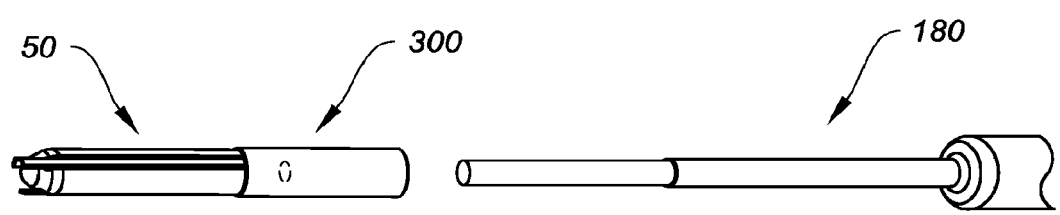
FIG. 6B shows a delivery tool with the inserter tool and device of FIG. 6A.

FIG. 6A shows an inserter tool 300 with the device 50 of FIGS. 5A and 5B. In addition, FIG. 6B shows the inserter tool 300 of FIG. 6A with delivery tool 180. As shown in FIG. 6A, the inserter tool 300 is implemented with its projections 308 extending inside and down the length of the flutes 62 of the implantable device 50. FIG. 6B shows the inserter tool 300 fully engaged with the implantable device 50 and can be used with the delivery tool 180 (previously shown above with reference to FIGS. 3E and 3F). As shown, the projections 308 may be deployed to cover the entire length of the flutes 62 to provide the maximum protection to the implantable device 50 during implantation. The projections 308 may be configured to be independently operable to allow directional control over the flow of material to be injected around the device 50.

Figure 7A:
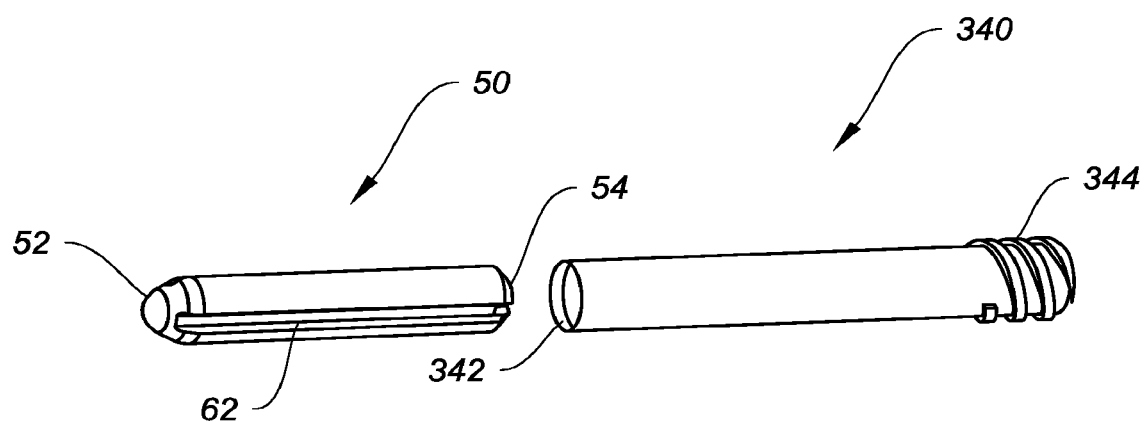
FIG. 7A shows the device of FIGS. 5A and 5B with an injection port.
Figure 7B:
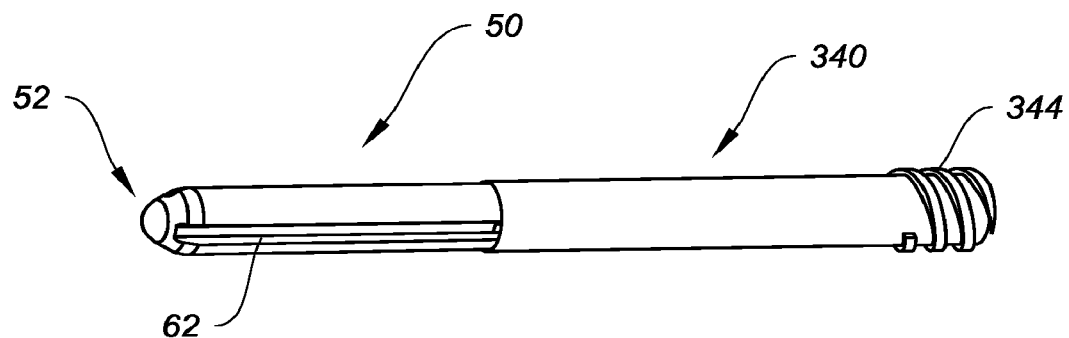
FIG. 7B shows the device of FIGS. 5A and 5B with the injection port attached to the device.

FIG. 7A shows the implantable device 50 of FIGS. 5A and 5B along with an injection port 340 that can be employed with the device 50. FIG. 7B shows the implantable device of FIGS. 5A and 5B connected to the injection port 340. As shown, an injection port 340 can be directly attached to the implantable device 50. As shown in FIGS. 7A and 7B, a device-engaging portion 342 of the injection port 340 can be attached to the implantable device 50. The device-engaging portion 342 of the injection port 340 and the second, trailing end 54 of the implantable device 50 may both be shaped to provide complementary mating surfaces for attachment (e.g., slightly tapered). Additionally, the device-engaging portion 342 may include a threaded section that complements a threaded section (not shown) on the second trailing end 54 of the device 50 in order to provide for a more secure connection. The injection port 340 can further include an injection connecting end 344 on the opposite end from the device-engaging portion 342 for engaging an injection system of a flowable material.

The injection port 340 allows for the introduction of a flowable material into and along the recesses 62 of the implantable device 50. As FIG. 5B illustrates, portions of the recesses 62 at the second, trailing end 54 are grooved with a larger depth than the remainder of the recess 62, in order to facilitate flow of the flowable material from its injection port into the recesses 62.

Other variations contemplated but not shown here include the addition of a shoulder or flange on the second, trailing end 54 of the implantable device 50 in order to provide a mechanism for cortical bone contact. The shoulder or flange would create an interference fit with the cortical bone.

The implantable device 50 of the present disclosure may be used to repair bone defects in a joint region such as the knee, shoulder, ankle, hip or other joint of the patient's body. The implantable devices may be useful, for example, in repairing an insufficiency fracture of a bone at a joint.

While the implantable devices 50 have been described as being used with an injectable or flowable material, it is understood, however, that these implants shown and described herein may be used alone without any injectable or flowable material if so desired.

Figure 8:
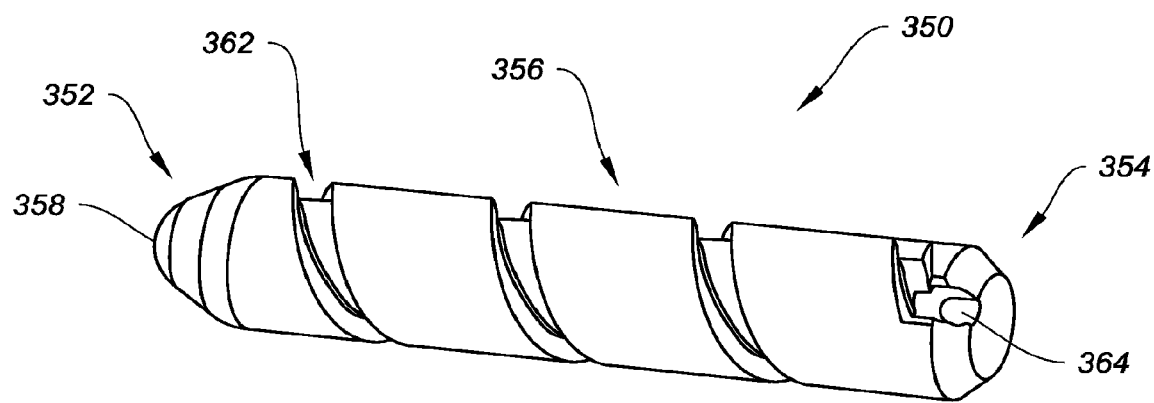
FIG. 8 illustrates yet another exemplary embodiment of an implantable device of the present disclosure.

FIG. 8 illustrates yet another exemplary embodiment of an implantable device 350 of the present disclosure. Implantable device 350 shares the same features as implantable device 50, with like elements being represented by the same numeral following the prefix "3". As shown, implantable device 350 can include a main body 356 extending between a first, leading end 352 and a second, trailing end 354. The first, leading end 352 of the implantable device 350 can include a tapered nose or tip 358 to facilitate ease of insertion to the target site. If so desired, however, the tip 358 may also be rounded or it may be flattened. In addition, a surface feature may be present on the main body 356 for enhanced bone tissue engagement with the target site, as previously mentioned.

Like implantable device 10 and 50, the implantable device 350 may further be augmented with a flowable material, such as a hardening material like a bone cement or augmentation material, such as a bone void filler, as previously described, other biological agent, or an osteoconductive, osteoinductive and/or osteogenic agent like a bone graft material. The flowable material may be introduced around the implantable device, and/or apart from the implantable device but at the affected bone region, such as into the lower region of a defect like a bone marrow lesion.

As shown, the main body 356 can be substantially solid and may include a recess or flute 362 extending around the periphery of the implantable device 350. The flute 362 may be a depressed region of the main body 356, and allow flowable material to be contained around the periphery of the device 350. The flowable material may be introduced at a single port 364 represented by the opening where the recess 362 meets the second, trailing end 354 of the implantable device 350.

Implantable device 350 may have a shape other than cylindrical, as described previously with devices 10 and 50. Furthermore, like devices 10 and 50, implantable device 350 may be formed of a bone material such as allograft or cadaver bone, including cortical, cortico-cancellous, bi-cortical, tri-cortical, or sesamoid bone material.

Figure 9:
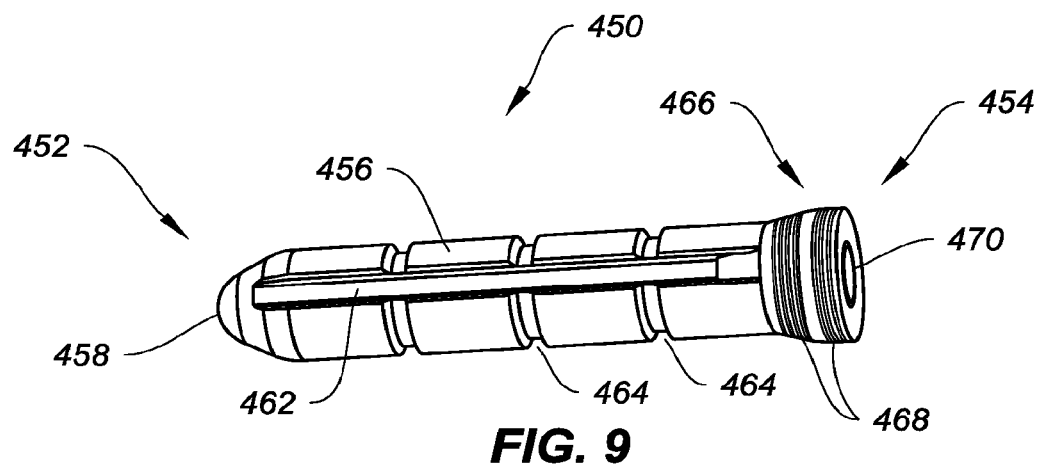
FIGS. 9 and 10 illustrated yet even more exemplary embodiments of implantable devices of the present disclosure.
Figure 10:
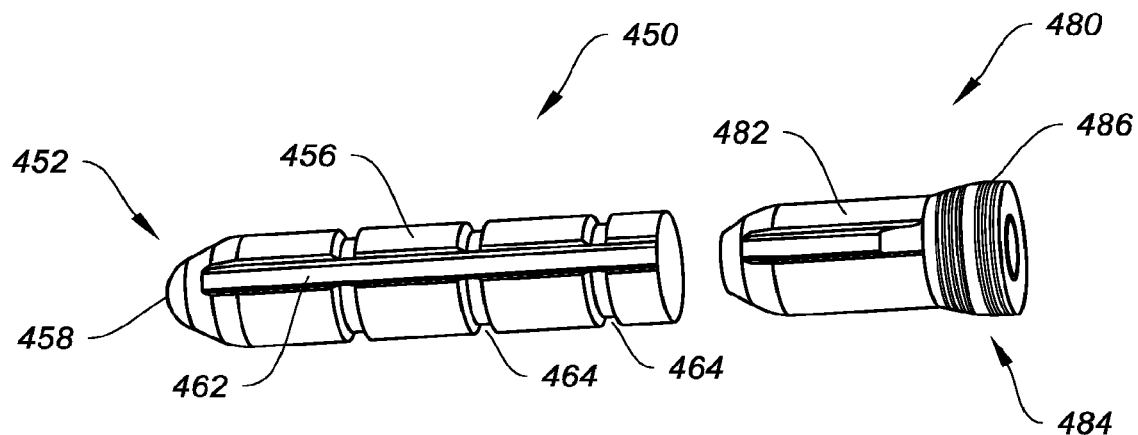

FIGS. 9 and 10 illustrated yet even more exemplary embodiments of implantable devices of the present disclosure. As shown in FIG. 9, implantable device 450 shares similar features with implantable device 50, with like elements being represented by the same numeral following the prefix "4". As shown, implantable device 450 can include a main body 456 extending between a first, leading end 452 and a second, trailing end 454. The first, leading end 452 of the implantable device 450 can include a tapered nose or tip 458 to facilitate ease of insertion to the target site. If so desired, however, the tip 458 may also be rounded or it may be flattened. In addition, a surface feature may be present on the main body 456 for enhanced bone tissue engagement with the target site, as previously mentioned.

Like implantable devices 10, 50 and 350, the implantable device 450 may further be augmented with a flowable material, such as a hardening material like a bone cement or augmentation material, such as a bone void filler, as previously described, other biological agent, or an osteoconductive, osteoinductive and/or osteogenic agent like a bone graft material. The flowable material may be introduced around the implantable device, and/or apart from the implantable device but at the affected bone region, such as into the lower region of a defect like a bone marrow lesion.

As shown, the main body 456 can be substantially solid and may include recesses or flutes 462 extending longitudinally along the periphery of the implantable device 450. Extending laterally around the periphery of the implantable device 450 are lateral recesses or flutes 464. The flutes 462, 464 may be depressed regions of the main body 456, and allow flowable material to be contained around the periphery of the device 450.

Implantable device 450 may have a shape other than cylindrical, as described previously with devices 10, 50 and 350. Furthermore, like devices 10, 50 and 350, implantable device 450 may be formed of a bone material such as allograft or cadaver bone, including cortical, cortico-cancellous, bi-cortical, tri-cortical, or sesamoid bone material.

In addition, the main body 456 may include a widened shoulder or flange portion 466 having threads 458 on a portion thereon at the second, trailing end 454. This flange portion 466 provides a mechanism for cortical bone contact. The shoulder or flange portion 466 would create an interference fit between the implantable device 450 and cortical bone. A tool-engaging opening 470 may also be provided at the second, trailing end 454 for engaging an insertion tool. The opening 470 may be threaded, for example.

FIG. 10 represents an alternative embodiment of the implantable device 450 of FIG. 9 whereby the flanged portion is a cap 480 that is a separate component from the main body 456 of the implantable device 450. As shown, the cap 480 may include a main body 482 extending from the flanged portion 484, on which there may be threads 486. Though not shown, the cap 480 may also include a tool-engaging opening for receiving an insertion tool. The cap 480 and implantable device 450 may engage each other in an interference fit, for example.

It is contemplated that a plug or cap may be provided with implantable devices 10 described above in order to seal off the central opening 30 and thereby prevent any flowable material contained within to leak out. Furthermore, a flanged portion may be provided with any one of the implantable devices 10, 50, 350 described above in order to provide a mechanism for attaching to cortical bone.

Another contemplated embodiment would provide a partially threaded, partial press-fit implantable device whereby the implantable device can be first implanted by press-fitting, then removing the insertion tool from the device and turning the device in place so as to thread the device further into the insertion bore.

For all of the implantable devices 10, 50, 350, 450 described herein, it is also possible to first deposit an aliquot of flowable material into a predrilled bore prior to inserting the implantable device 10, 50, 350, and 450. In this exemplary method, the insertion of the device would push excess flowable material out and around the device 10, 50, 350, 450, settling into the recess or flute of the device.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A method of treating a bone defect, comprising:
   providing or receiving an implantable device having:
      a first, leading end;
      a second, trailing end;
      a main body extending between the leading and trailing ends;
      a plurality of fins on the main body;
      a plurality of recesses on the main body, wherein each recess is separated by an adjacent pair of the fins;
      a central opening extending through a length of the main body; and
      at least one channel residing in each recess, each channel in fluid communication with the central opening to allow extrusion of a flowable material from the central opening to outside the main body;
      wherein the device is formed of an allograft material;
   inserting the device in or adjacent to the bone defect with an inserter tool, the inserter tool including a plurality of finger-like projections, wherein each of the finger-like projections is slideably received by a corresponding one of the recesses prior to insertion, and wherein each finger-like projection is capable of separate and independent sliding movement with respect to the other finger-like projections;
   introducing a flowable material through the central opening and out of the at least one channel in one or more of the plurality of recesses; and
   allowing the flowable material to extrude away from the device.

2. The method of claim 1, wherein the finger-like projections of the inserter tool occlude the at least one channel in each recess.

3. The method of claim 1, wherein the leading end of the device comprises a tapered tip.

4. The method of claim 1, wherein the defect is near an articular surface of a joint.

5. The method of claim 4, wherein the joint is a knee joint.

6. The method of claim 1, wherein the bone defect is a bone marrow lesion.

7. The method of claim 1, wherein the flowable material is a bone cement.

8. A method of treating a bone defect, comprising:
   inserting an implantable device in or adjacent to the bone defect with an inserter tool, the implantable device having a leading end, a trailing end, a main body extending between the leading and trailing ends, a lumen extending within at least a portion of the main body, a plurality of depressed regions extending along the main body, and at least one channel located within each of the depressed regions and in fluid communication with the lumen, wherein each of the depressed regions is engaged with one of a plurality of finger-like projections of the inserter tool, and wherein each finger-like projection is capable of separate and independent sliding movement with respect to the other finger-like projections;
   slideably retracting at least one of the finger-like projections to uncover one or more of the channels;
   introducing a flowable material through the lumen and out of the one or more uncovered channels; and
   allowing the flowable material to extrude away from the implantable device.

9. The method of claim 8, wherein the implantable device is at least partially formed of an allograft material.

10. The method of claim 8, wherein the defect is adjacent to an articular surface of a joint.

11. The method of claim 8, wherein the implantable device is inserted in or adjacent to the bone defect such that the leading end of the implantable device does not breach an articular surface of a joint.

12. A method for treatment of a bone defect, comprising:
providing or receiving an implantable device having a leading end, a trailing end, a main body extending between the leading and trailing ends, a lumen extending within at least a portion of the main body, and at least one channel in fluid communication with the lumen to allow extrusion of a flowable material from the lumen to outside the main body, wherein the implantable device includes a plurality of recesses extending along a longitudinal axis of the main body, the at least one channel being located within one of the recesses;
engaging the implantable device with an inserter tool, the inserter tool comprising a shaft having an implantable device-engaging portion at a first end and a handle portion at a second end, wherein the implantable device-engaging portion of the inserter tool includes a plurality of movable finger-like projections, wherein engaging the implantable device with the inserter tool comprises sliding each of the finger-like projections into one of the recesses to occlude the at least one channel;
inserting the implantable device in or adjacent to the bone defect;
introducing a flowable material through the lumen and out of the at least one channel; and
allowing the flowable material to extrude away from the implantable device;
wherein each finger-like projection is capable of separate and independent sliding movement with respect to the other projections to control access to the at least one channel and a direction in which the flowable material is extruded.

13. The method of claim 12, wherein the plurality of recesses are separated by a plurality of fins.

14. The method of claim 12, wherein the implantable device is at least partially formed of a bone material.

15. The method of claim 12, wherein the leading end of the implantable device includes a tapered tip.

* * * * *